US012016695B2

(12) United States Patent
Harkema et al.

(10) Patent No.: US 12,016,695 B2
(45) Date of Patent: *Jun. 25, 2024

(54) DETERMINATION OF STIMULATION PARAMETERS FOR MUSCLE ACTIVATION

(71) Applicant: University of Louisville Research Foundation, Inc., Louisville, KY (US)

(72) Inventors: Susan J. Harkema, Louisville, KY (US); Enrico Rejc, Louisville, KY (US); Samineh Mesbah, Louisville, KY (US)

(73) Assignee: University of Louisville Research Foundation, Inc., Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/175,874

(22) Filed: Feb. 28, 2023

(65) Prior Publication Data
US 2023/0200713 A1   Jun. 29, 2023

Related U.S. Application Data

(63) Continuation of application No. 16/906,443, filed on Jun. 19, 2020, now Pat. No. 11,622,711.

(60) Provisional application No. 62/864,358, filed on Jun. 20, 2019.

(51) Int. Cl.
| | |
|---|---|
| A61B 5/395 | (2021.01) |
| A61N 1/36 | (2006.01) |
| G06F 17/14 | (2006.01) |
| G16H 20/30 | (2018.01) |
| G16H 50/70 | (2018.01) |

(52) U.S. Cl.
CPC .......... *A61B 5/395* (2021.01); *A61N 1/36062* (2017.08); *A61N 1/36135* (2013.01); *G06F 17/142* (2013.01); *G16H 20/30* (2018.01); *G16H 50/70* (2018.01)

(58) Field of Classification Search
CPC .... A61B 5/395; A61B 5/389; A61N 1/36062; A61N 1/36135
See application file for complete search history.

(56) References Cited

U.S. PATENT DOCUMENTS

| | | | |
|---|---|---|---|
| 2017/0173326 A1* | 6/2017 | Bloch | A61N 1/36139 |
| 2018/0093093 A1* | 4/2018 | Courtine | A61B 5/24 |

* cited by examiner

*Primary Examiner* — Paula J Stice
(74) *Attorney, Agent, or Firm* — Dentons Bingham Greenebaum LLP; Brian W. Chellgren

(57) ABSTRACT

Computer-implemented systems and methods for determining epidural spinal stimulation parameters that promote muscle activation use spectral analysis and machine learning techniques to characterize electromyography data.

17 Claims, 15 Drawing Sheets
(8 of 15 Drawing Sheet(s) Filed in Color)

DETERMINATION OF STIMULATION PARAMETERS FOR MUSCLE ACTIVATION

CROSS-REFERENCE TO RELATED APPLICATIONS

This application is a continuation of U.S. patent application Ser. No. 16/906,443, filed Jun. 19, 2020, now issued as U.S. Pat. No. 11,622,711, which claims the benefit of U.S. provisional patent application Ser. No. 62/864,358, filed Jun. 20, 2019, each of which is incorporated herein by reference.

FIELD OF THE INVENTION

Computer-implemented systems and methods for determining epidural spinal stimulation parameters that promote muscle activation use spectral analysis and machine learning techniques to characterize electromyography data.

BACKGROUND OF THE INVENTION

Individuals with motor complete spinal cord injury (SCI) are unable to stand, walk, or move their lower limbs voluntarily; this condition drastically affects their quality of life and implies severe limitations for functional recovery. In the last years, there has been increasing evidence that the combination of lumbosacral spinal cord epidural stimulation (scES) and activity-based training that includes standing and stepping practice can promote the recovery of standing, walking and volitional leg movements in chronic, clinically motor complete and incomplete SCI individuals. To date, the prevailing view is that scES modulates the excitability of lumbosacral spinal circuitry by recruiting afferent fibers carrying somatosensory information. This excitability modulation, in turn, can enable the spinal circuitry to generate appropriate muscle activation patterns in response to sensory information, and can also allow residual functionally silent descending input to modulate standing and stepping activation patterns.

The ability to stand with independent lower limb extension is a key achievement toward the recovery of functional mobility, and was consistently observed in all three motor complete SCI individuals that subsequently recovered over ground stepping and walking. We showed that the appropriate selection of individual-specific scES parameters is crucial to promote standing with independent lower limb extension in this population. The guidelines proposed for selecting a sub-set of electrode configurations to be tested for facilitating standing include adjusting cathodes (active electrodes) positon in order to target primarily extensor muscle groups according to the individualized map of motor pools activation. Also, the use of multiple interleaving programs represents an important advantage compared to the use of a single program, as it allows to access different locations of the spinal circuitry with different intensities.

However, to date there are no available algorithms or procedures that suggest the exact set of parameters to be applied for facilitating standing using tonic scES. In addition, the characteristics of muscle activation patterns leading to independent standing remain poorly understood. We observed that electromyography (EMG) patterns that alternate bursts and negligible activation result in poor standing ability. On the other hand, the overall continuous (i.e. non-rhythmic) co-activation of several lower limb muscles is detected during standing with independence of lower limb extension. However, similar continuous activation patterns have been observed also when external assistance for lower limb extension was required to stand. Understanding the characteristics of muscle activation patterns leading to independent standing can be of great importance for developing machine learning models capable of contributing to the selection of appropriate scES parameters.

SUMMARY

Embodiments of the present invention relate to a novel framework for EMG data processing that implements spectral analysis and machine learning methods for characterizing EMG activity resulting in independent (i.e., unassisted) or assisted standing, and for identifying which of the tested sets of stimulation parameters promote muscle activation more effective for standing. The inventors determined which spectral analysis method is more effective for identifying frequency-domain EMG features that characterize independent standing promoted by scES in humans with clinically motor complete SCI. The inventors then integrated EMG frequency- and time-domain features in the computational model and tested its ability to accurately classify independent and assisted standing. Also, the physiological characteristics of EMG activity resulting in assisted and independent standing were defined. Finally, the inventors applied the proposed framework on EMG datasets collected while research participants were testing different scES stimulation parameters for standing in order to rank the effectiveness of the muscle activation generated.

It will be appreciated that the various systems and methods described in this summary section, as well as elsewhere in this application, can be expressed as a large number of different combinations and subcombinations. All such useful, novel, and inventive combinations and subcombinations are contemplated herein, it being recognized that the explicit expression of each of these combinations is unnecessary.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A better understanding of the present invention will be had upon reference to the following description in conjunction with the accompanying drawings.

DETAILED DESCRIPTION OF THE PREFERRED EMBODIMENTS

Figure 1:
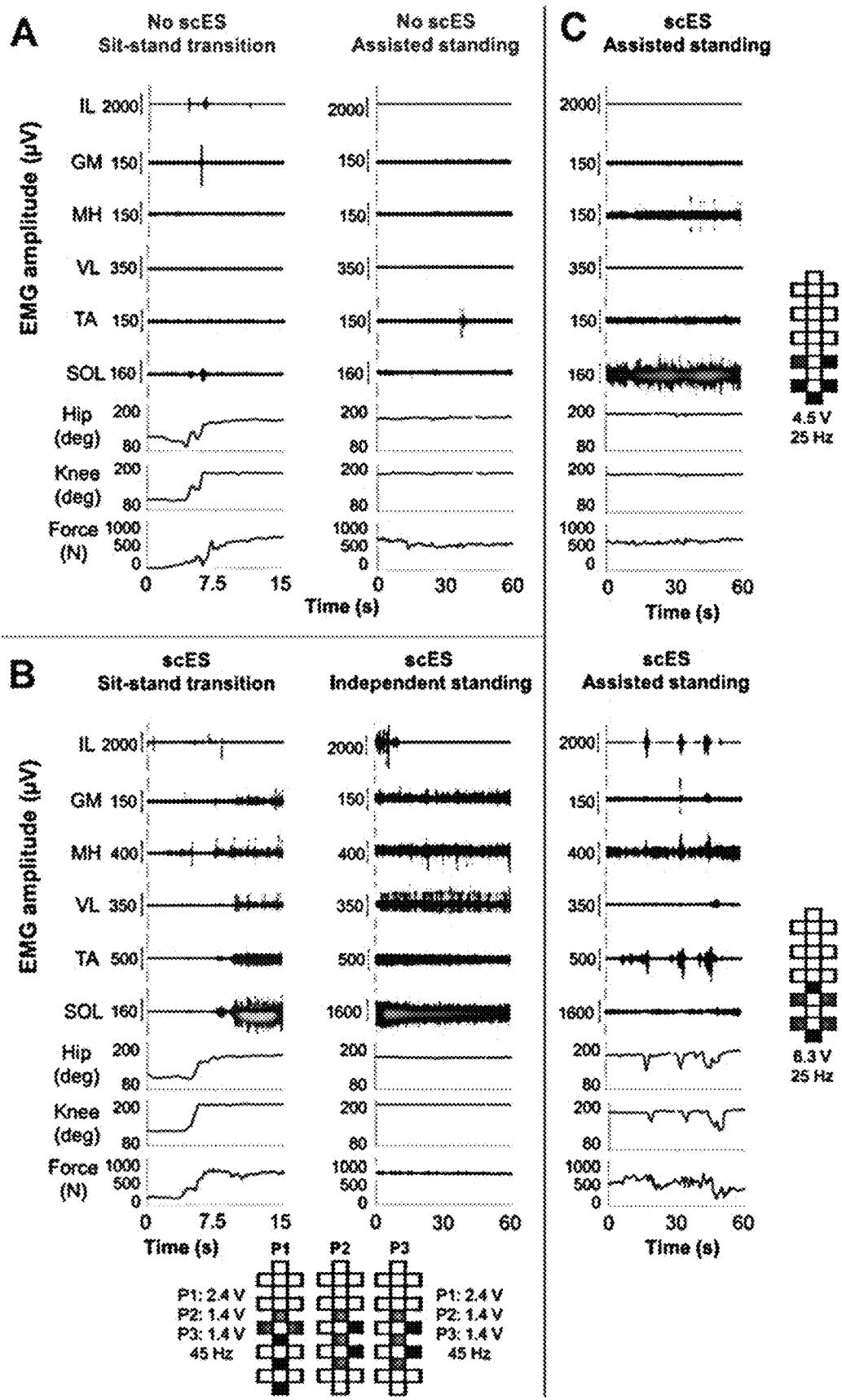
FIG. 1 depicts EMG, lower limb joint angles and ground reaction forces during sit-to-stand transition and during standing. EMG, hip and knee joint angle, and ground reaction forces recorded form research participant A59 during: (A) sit-to-stand transition and standing with external assistance for hips and knees extension (assisted standing) without scES; (B) sit-to-stand transition and independent standing using scES; the participant held the hands of a trainer for balance control; and (C) assisted standing with scES resulting from an overall continuous activation pattern (top) and from an EMG pattern characterized by the alternation of EMG bursts and little activation. Stimulation amplitude, frequency and electrode configuration (cathodes in black, anodes in red, and inactive in white) are reported for each standing condition. In (B), the participant was stimulated with 3 programs delivered sequentially at 15 Hz, resulting in an ongoing 45 Hz stimulation frequency. EMG was recorded from the following muscles of the right lower limb: IL, iliopsoas; GL, gluteus maximus; MH, medial hamstring; VL, vastus lateralis; TA, tibialis anterior; SOL, soleus.

For the purposes of promoting an understanding of the principles of the invention, reference will now be made to selected embodiments illustrated in the drawings and specific language will be used to describe the same. It will nevertheless be understood that no limitation of the scope of the invention is thereby intended; any alterations and further modifications of the described or illustrated embodiments, and any further applications of the principles of the invention as illustrated herein are contemplated as would normally occur to one skilled in the art to which the invention relates. At least one embodiment of the invention is shown in great detail, although it will be apparent to those skilled in the relevant art that some features or some combinations of features may not be shown for the sake of clarity.

Any reference to "invention" within this document is a reference to an embodiment of a family of inventions, with no single embodiment including features that are necessarily included in all embodiments, unless otherwise stated. Furthermore, although there may be references to "advantages" provided by some embodiments of the present invention, other embodiments may not include those same advantages, or may include different advantages. Any advantages described herein are not to be construed as limiting to any of the claims.

Specific quantities (spatial dimensions, dimensionless parameters, etc.) may be used explicitly or implicitly herein, such specific quantities are presented as examples only and are approximate values unless otherwise indicated. Discussions pertaining to specific compositions of matter, if present, are presented as examples only and do not limit the applicability of other compositions of matter, especially other compositions of matter with similar properties, unless otherwise indicated.

Standing Motor Patterns with and without scES.

Research participants required external assistance for lower limb extension when scES was not provided. Limited EMG activity was generally observed in response to the assisted sit-to-stand transition, and negligible EMG was recorded during standing with external assistance for hips and knees extension (assisted standing; FIG. 1A). When scES parameters for standing were applied, little activity and no movement was directly induced in sitting (FIG. 1B). Without any change in stimulation parameters, sensory information related to the sit-to-stand transition and loading of the legs resulted in the generation of motor patterns with different characteristics (FIGS. 1B and 1C). It was consistently observed that standing with independence of hip and knee extension (independent standing) is enabled by overall continuous (i.e. non-rhythmic) EMG activity (FIG. 1B). However, continuous EMG patterns can also be insufficient for achieving independent standing (FIG. 1C, top). On the other hand, the alternation between EMG bursts and negligible activity in lower limb muscles always resulted in assisted standing (FIG. 1C, bottom).

Time- and Frequency-Domain EMG Features can Accurately Classify Assisted Versus Independent Standing.

Figure 2:
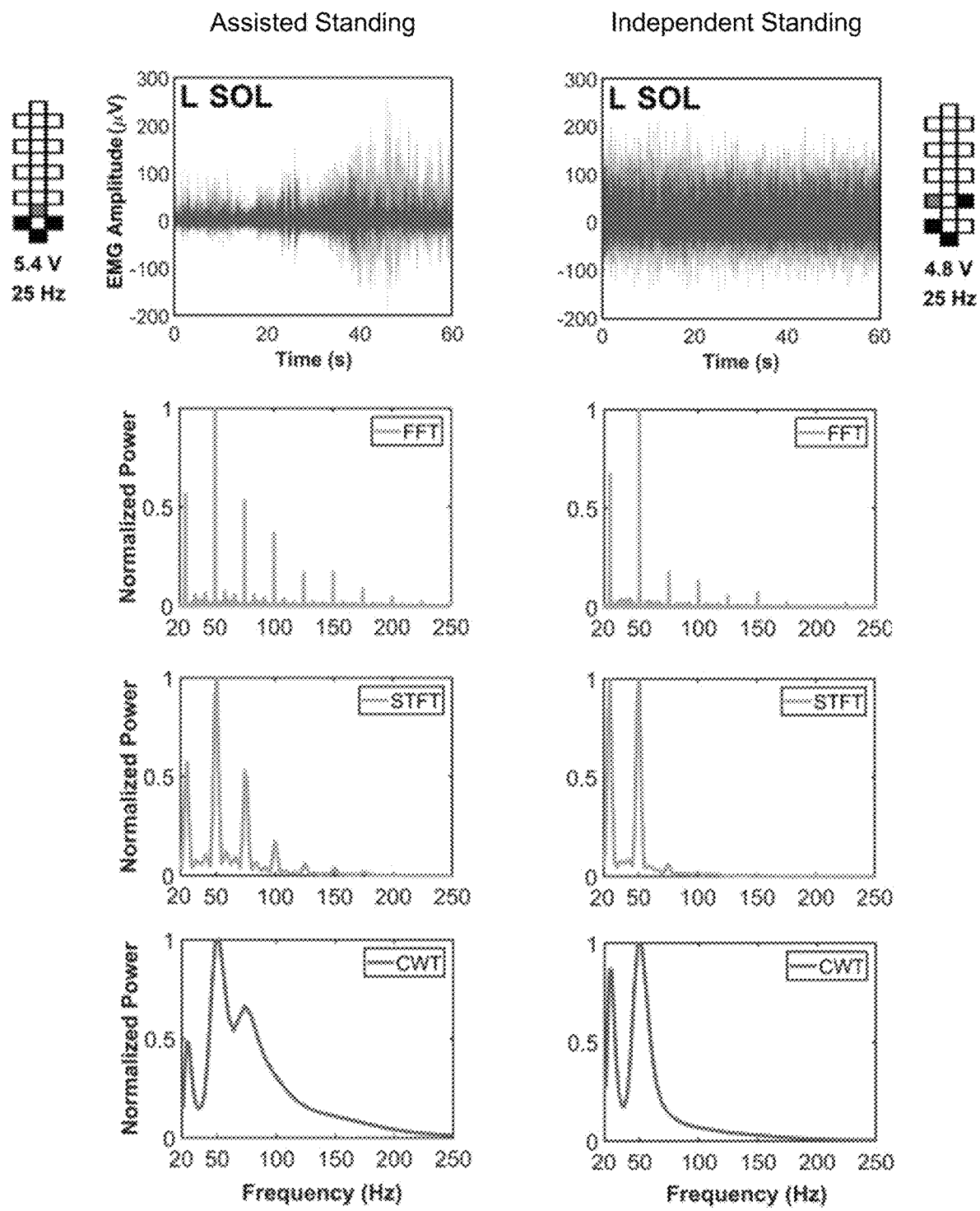
FIG. 2 is a series of charts depicting the spectral power density of EMG collected during assisted standing (left column) and independent standing (right column). The topmost charts depict EMG activity recorded from the left soleus (L SOL) of research participant A45 during assisted standing and independent, respectively, with epidural stimulation. The below charts depict spectral power density generated by Fast Fourier Transform (FFT), Short-Time Fourier Transform (STFT) and Continuous Wavelet Transform (CWT). Stimulation amplitude, frequency and electrode configuration (cathodes in black, anodes in red, and inactive in white) are reported.

Two EMG variables (EMG total power and pattern variability) were initially included in the proposed data processing framework aimed at classifying assisted and independent standing. This approach led to a classification accuracy for assisted and independent standing equal to 83.7% when all investigated muscles were considered for analysis. To improve this classification accuracy, we explored the inclusion of frequency-domain EMG features in the computational model. An initial step was devoted to the selection of an effective analysis method for EMG activity promoted by scES. When exemplary EMG signals recorded during assisted and independent standing were considered for analysis (FIG. 2), Fast Fourier Transform (FFT) and Short-Time Fourier Transform (STFT) primarily highlighted the content of frequencies related to scES frequency (25 Hz) and its harmonics. However, frequency values in between the 25 Hz spikes are suppressed in the FFT and STFT panels. On the other hand, Continuous Wavelet Transform (CWT) shown in the bottom panels in each column highlighted relevant frequency content that was not related to scES frequency. More specifically, the frequency content between the application of scES at 25 Hz correspond to the frequency content of the physiological response of the muscle to the stimulation. Also, the power of EMG signal collected during independent standing tended to be shifted toward lower frequency bins compared to that recorded during assisted standing. We then applied these three signal analysis methods on all EMG data collected during assisted and independent standing events from the 11 research participants considered in this study as shown in Table 1.

TABLE 1

Number of events considered for each research participant and standing condition.

| Participant | Hips and knees assisted (N) | Hips assisted knees independent (N) | Hips and knees independent (N) | One knee assisted (N) |
|---|---|---|---|---|
| B13 | 70 | 11 | 0 | 0 |
| B07 | 36 | 10 | 0 | 0 |
| A45 | 13 | 7 | 10 | 6 |
| A53 | 13 | 0 | 14 | 3 |
| B23 | 4 | 12 | 12 | 0 |
| A59 | 8 | 5 | 12 | 30 |
| B30 | 1 | 3 | 59 | 2 |
| A60 | 2 | 7 | 20 | 4 |
| A68 | 74 | 2 | 0 | 5 |
| A41 | 47 | 0 | 0 | 21 |
| B21 | 48 | 0 | 0 | 0 |
| Total standing events (N) | 316 | 57 | 127 | 71 |

After normalization, dimension reduction and logarithmically transforming the EMG spectral feature values, the first three dimensions of standing data points (blue: independent standing; red: assisted standing) derived from the tested spectral analysis methods were plotted in FIG. 3A. The three analysis methods result in different distributions of the data points, and CWT tends to present a clearer visual discrimination between assisted and independent standing data points. These feature values were subsequently used as input for K-nearest neighbor (KNN) classification. As expected from the exemplary data analysis and from the data points presented in FIG. 3A, we observed that CWT-derived features promoted the highest classification accuracy for assisted versus independent standing compared to STFT- and particularly FFT-derived features (FIG. 3B).

Hence, CWT-derived data were integrated with time-domain EMG features (EMG total power and EMG pattern variability), resulting in a classification accuracy for assisted versus independent standing ranging from 94.4% to 97.1%, depending on the considered muscle(s) (FIG. 3C). This classification accuracy is higher and more consistent across examined muscles compared to when either frequency- or particularly time-domain EMG features alone were considered (FIGS. 3B and 3C). Based on the results reported in this section, CWT-derived data was also considered for further analysis aimed at describing the physiological characteristics of muscle activation during standing with scES.

Physiological Characteristics of Muscle Activation Resulting in Assisted or Independent Standing.

Figure 4A:
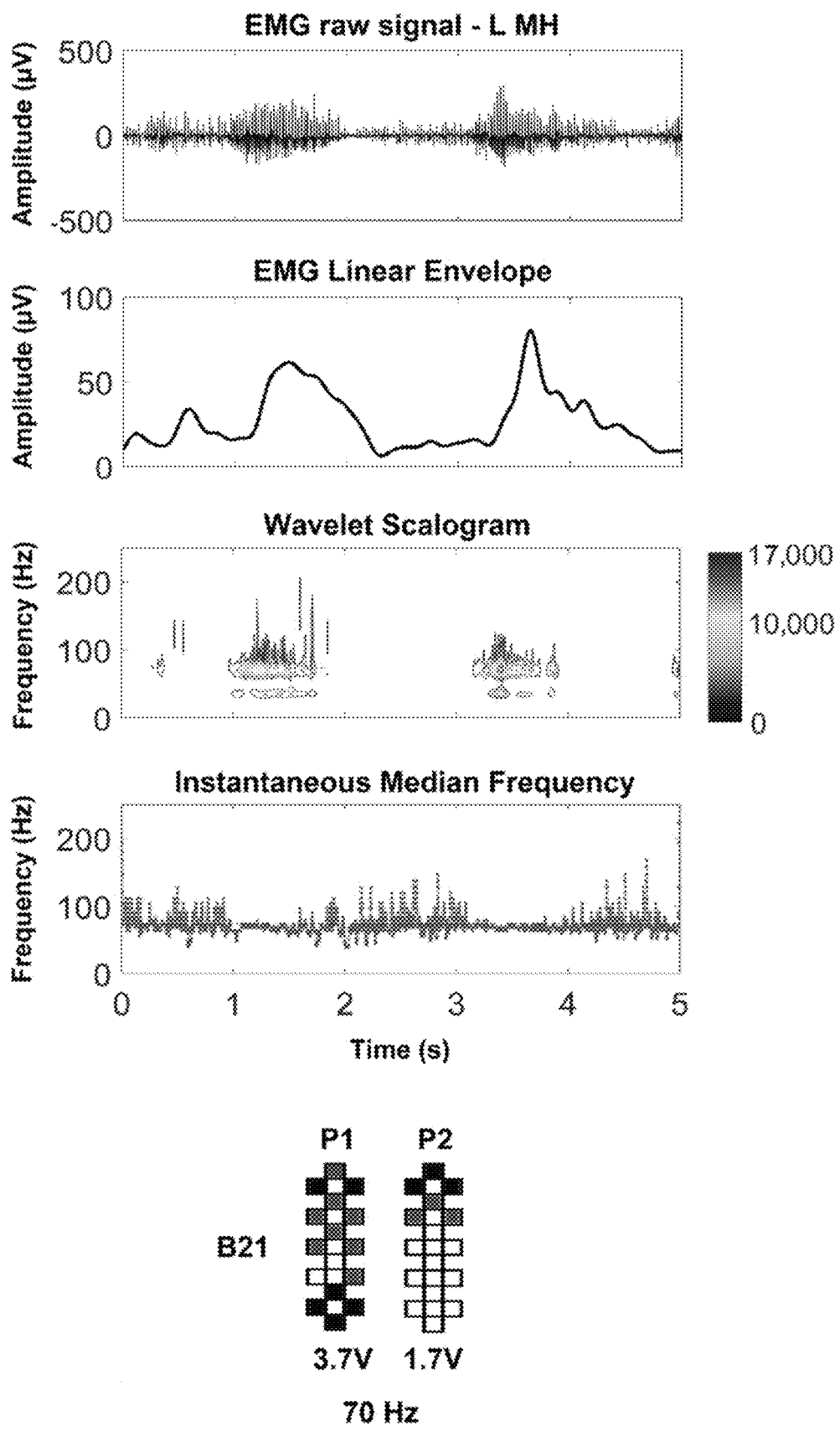
FIG. 4A depicts EMG-time and -frequency features characterizing exemplary assisted standing activation patterns. EMG activity recorded from the left medial hamstrings (L MH) during standing with self-assistance for balance and external assistance for hip and knee extension characterized by EMG bursts. For each standing condition, the EMG linear envelope, time-frequency power distribution of the signal (wavelet scalogram), and instantaneous median frequency are calculated from the plotted raw EMG. The wavelet scalogram is presented as contour plots, the power values of which are represented as colormaps, with the color scale showing the range of power values. Stimulation amplitude, frequency and electrode configuration (cathodes in black, anodes in red, and inactive in white) are reported.

Higher values of EMG pattern variability calculated from EMG linear envelope can characterize the muscle activation pattern consisting in the alternation between EMG bursts and lower activity (FIG. 4A; pattern variability=0.68), which results in poor, assisted standing. On the other hand, this feature does not discriminate between overall continuous EMG patterns resulting in assisted standing (FIG. 4B; pattern variability=0.23) or independent standing (FIG. 4C; pattern variability=0.22). CTW can provide additional information based on instantaneous EMG time- and frequency-domain features. For example, in case of the alternation between EMG bursts and limited activation, the maximum power variability is also relevant (FIG. 4A, Wavelet Scalogram; EMG maximum power variability=1.35) compared to the condition of assisted standing with continuous EMG pattern (FIG. 4B; EMG maximum power variability=0.35).

Figure 4B:
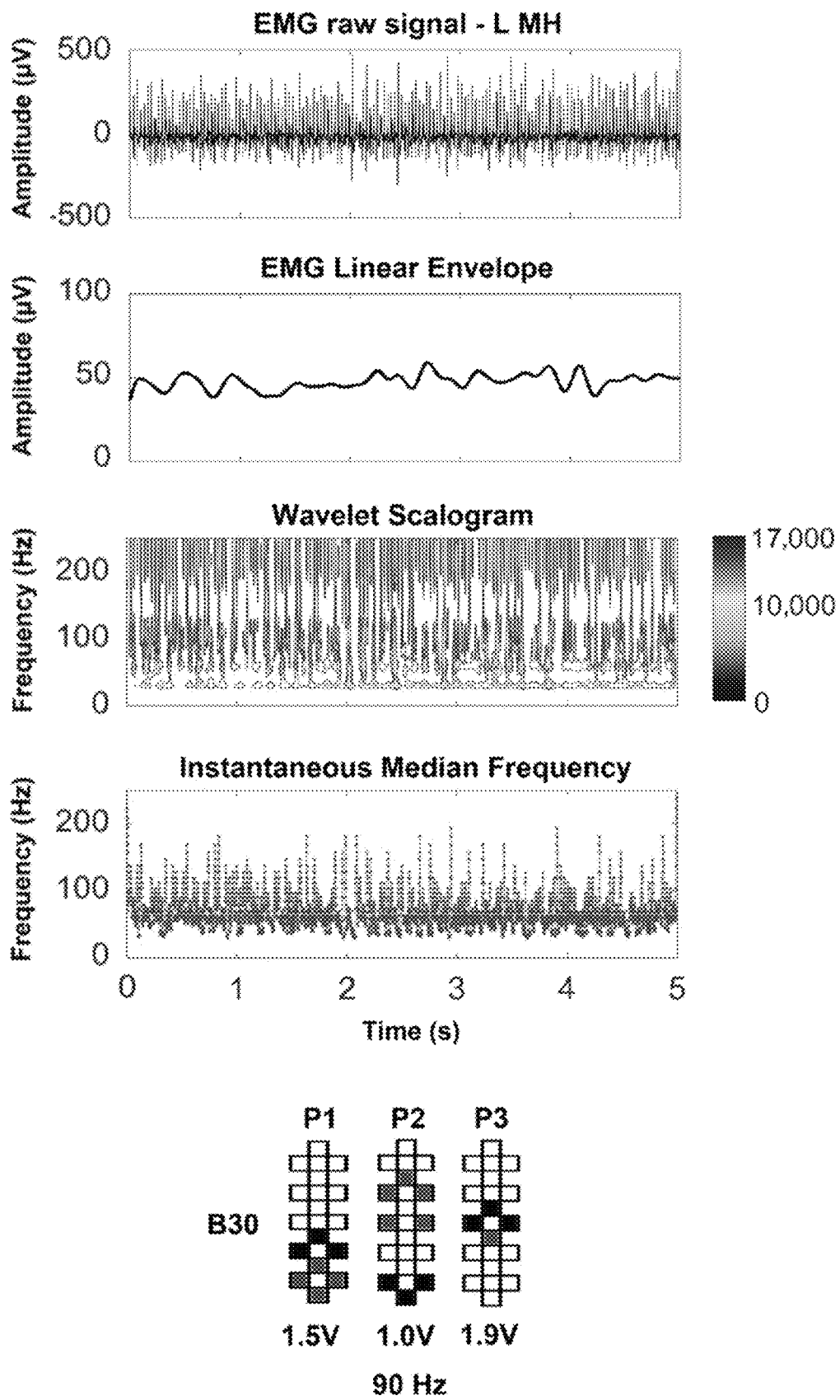
FIG. 4B depicts EMG-time and -frequency features characterizing exemplary assisted standing activation patterns. EMG activity recorded from the left medial hamstrings (L MH) during standing with self-assistance for balance and external assistance for hip and knee extension characterized by a EMG bursts or by b continuous EMG activity, as well as c during independent standing with self-assistance for balance. For each standing condition, the EMG linear envelope, time-frequency power distribution of the signal (wavelet scalogram), and instantaneous median frequency are calculated from the plotted raw EMG. The wavelet scalogram is presented as contour plots, the power values of which are represented as colormaps, with the color scale showing the range of power values. Stimulation amplitude, frequency and electrode configuration (cathodes in black, anodes in red, and inactive in white) are reported.
Figure 4C:
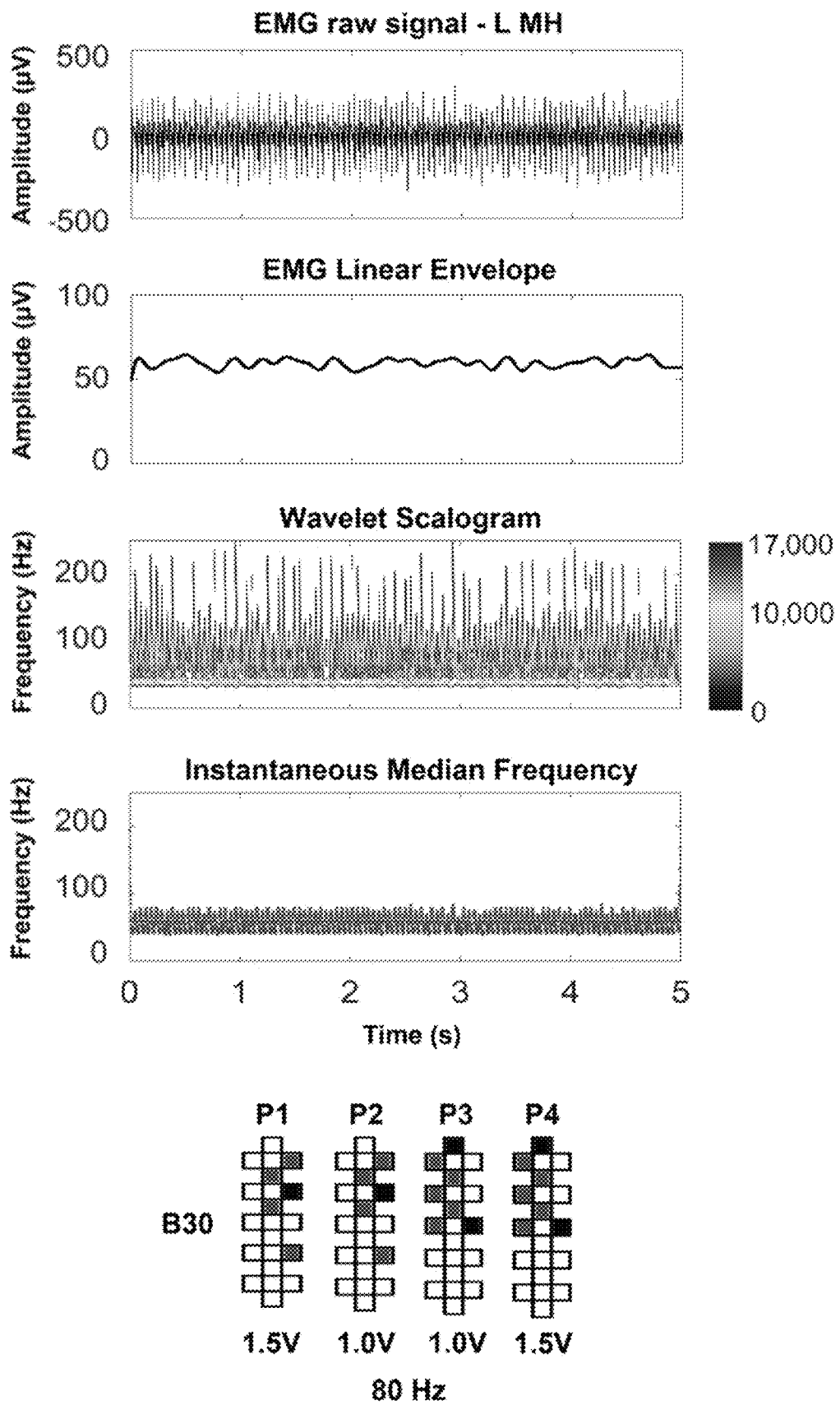
FIG. 4C depicts EMG-time and frequency features characterizing exemplary independent standing activation patterns. EMG activity recorded from the left medial hamstrings (L MH) during independent standing with self-assistance for balance characterized by continuous EMG activity. For each standing condition, the EMG linear envelope, time-frequency power distribution of the signal (wavelet scalogram), and instantaneous median frequency are calculated from the plotted raw EMG. The wavelet scalogram is presented as contour plots, the power values of which are represented as colormaps, with the color scale showing the range of power values. Stimulation amplitude, frequency and electrode configuration (cathodes in black, anodes in red, and inactive in white) are reported.

Differences in the CWT pattern can be observed also between the two similar continuous raw EMG activity recorded from the same individual during assisted and independent standing (FIGS. 4B and 4C, respectively). In particular, assisted standing (FIG. 4B) tended to present greater EMG maximum power variability (0.48), higher median frequency (70 Hz) and greater variability of median frequency (median frequency standard deviation=32 Hz) compared to EMG activity that resulted in independent standing (0.35, 59 Hz, and 20 Hz, respectively; FIG. 4C).

Figure 5:
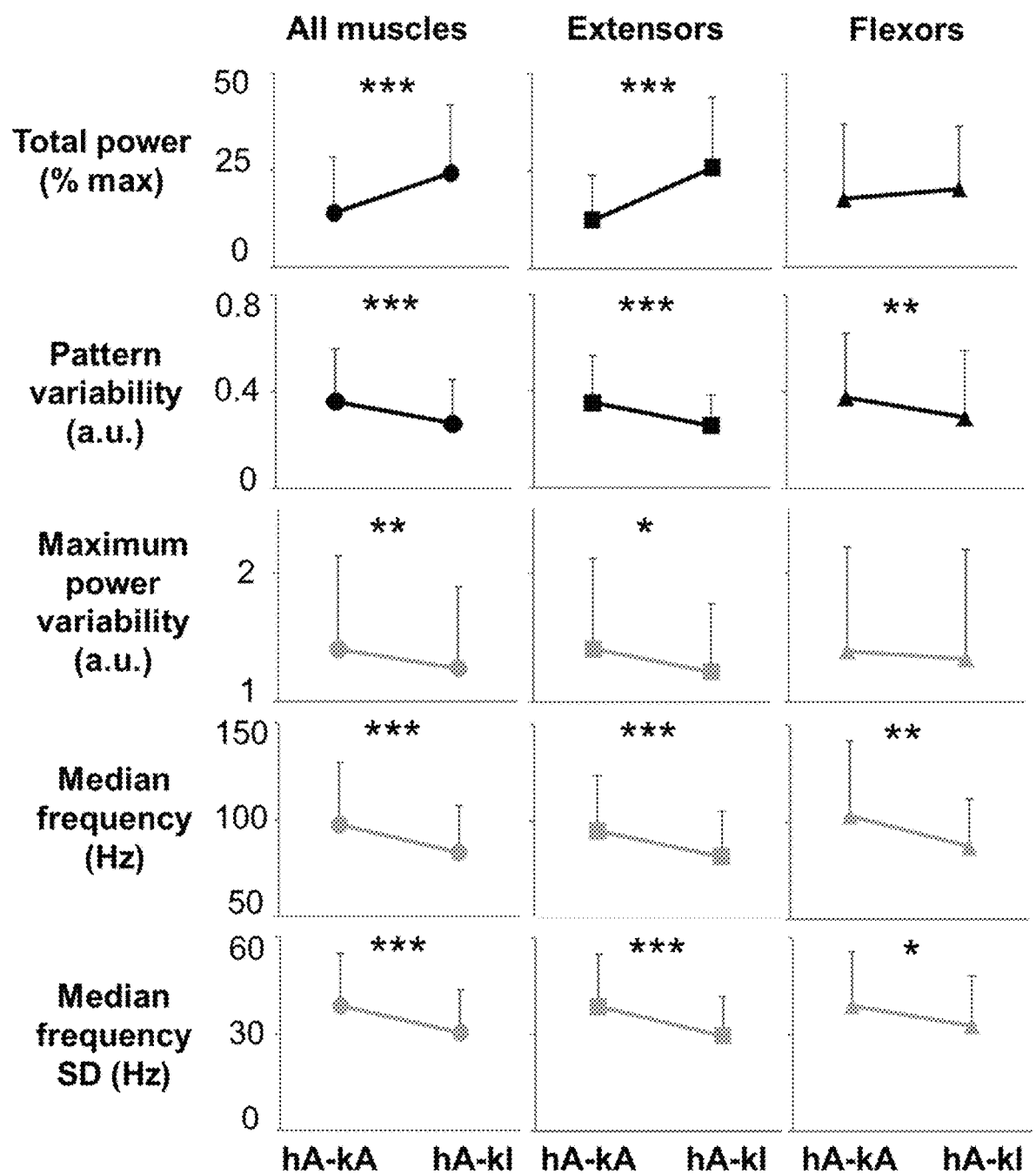
FIG. 5 depicts quantification of EMG-time and -frequency domain features collected during standing with knees assisted or standing with independent knees extension. Representative time- and frequency-domain EMG features collected during standing with external assistance for hips and knees extension (hA-kA), and during standing with hips assisted and independent knees extension (hA-kI). EMG features values were averaged among research participants (n=8) and among all investigated muscles (left and right soleus, medial gastrocnemius, vastus lateralis, rectus femoris, gluteus maximus, tibialis anterior and medial hamstring; total n=114), among primary extensor muscles (left and right soleus, medial gastrocnemius, vastus lateralis, rectus femoris, gluteus maximus; total n=80), or among primary flexor muscles (left and right tibialis anterior and medial hamstring; total n=32). Values are expressed as mean±standard deviation (SD). Differences were tested by Wilcoxon test. * $p<0.05$;  $p<0.01$; * $p<0.001$.

Paired comparisons (n=8) show that standing with independent knees extension was promoted by significantly higher EMG total power, lower pattern variability, lower maximum power variability, lower median frequency standard deviation (SD), and lower median frequency as compared to assisted standing (FIG. 5). These differences were more pronounced when all investigated muscles and primary extensor muscles were considered as compared to primary flexor muscles. The average stimulation frequency was similar between the two conditions (47±24 Hz for assisted standing and 51±27 Hz for independent knees extension; p=0.844).

Figure 9:
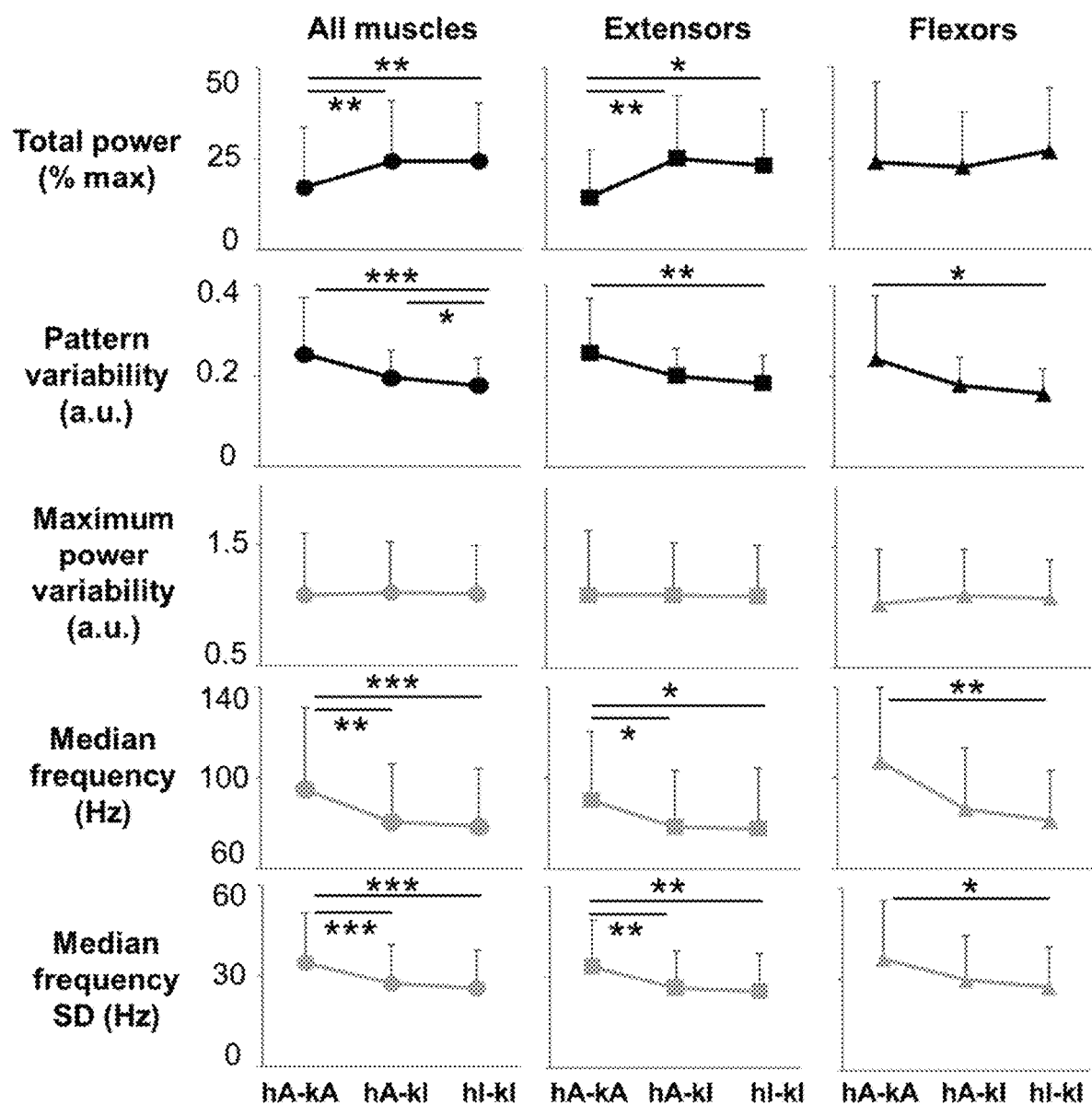
FIG. 9 depicts quantification of EMG-time and -frequency domain features collected during standing with different amount of external assistance. Representative time- and frequency-domain EMG features collected during standing with external assistance for hips and knees extension (hA-kA), during standing with hips assisted and independent knees extension (hA-kI), and during standing with independent hips and knees extension (hI-kI). EMG features values were averaged among research participants (n=5) and among all investigated muscles (left and right soleus, medial gastrocnemius, vastus lateralis, rectus femoris, gluteus maxim us, tibialis anterior and medial hamstring; total n=70), primary extensor muscles (left and right soleus, medial gastrocnemius, vastus lateralis, rectus femoris, gluteus maxim us; total n=50), or primary flexor muscles (left and right tibialis anterior and medial hamstring; total n=20). Values are expressed as mean±standard deviation (SD). Differences were tested by by either Repeated Measures Anova (and following multiple comparisons by Bonferroni's post hoc test) or by Friedman Test (and following multiple comparisons by Dunn's post hoc test), depending on the data distribution characteristics. * $p<0.05$;  $p<0.01$; * $p<0.001$.

We then performed a similar comparison including the 5 individuals who achieved assisted standing, standing with external assistance at the hips and independent knees extension, and independent standing (FIG. 9). No substantial differences were observed between standing conditions with hips assisted or hips independent while the knees achieved independent extension. On the other hand, these two standing conditions demonstrating independent knees extension were characterized by higher EMG total power, lower pattern variability, lower median frequency variability, and lower median frequency compared to standing with hips and knees assisted, showing the same trend already reported in FIG. 5. Also, the average stimulation frequency was similar across these three standing conditions (58±24 in assisted standing; 61±29 Hz in hips assisted and knees independent; 62±33 Hz in independent standing; p=0.182).

Figure 7:
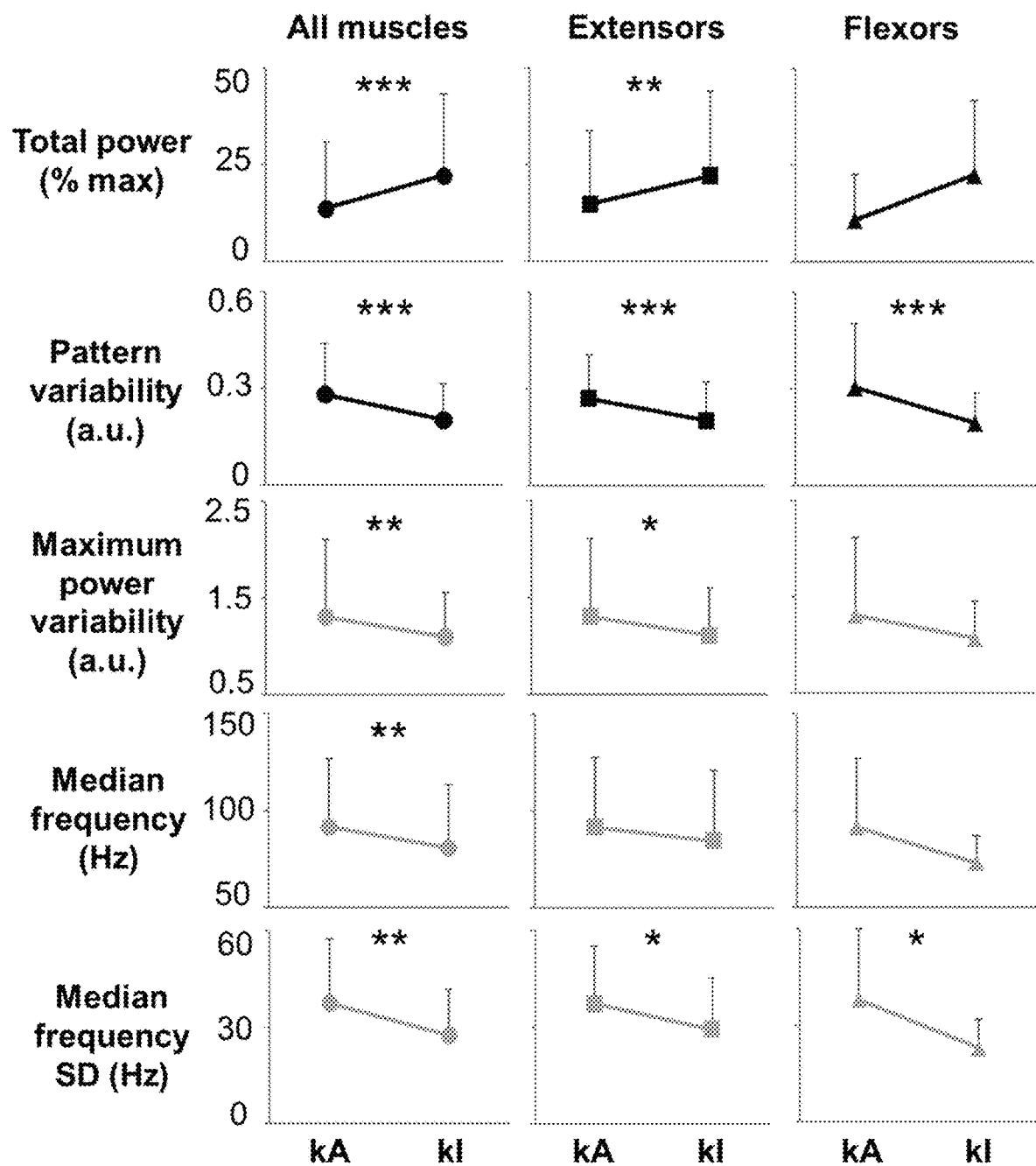
FIG. 7 depicts quantification of EMG-time and -frequency domain features collected during standing with one lower limb assisted for knee extension. Representative time- and frequency-domain EMG features collected during standing when one lower limb achieved independent extension (kI) while the contralateral limb required external assistance for knee extension (kA). EMG features values were averaged among research participants (n=7) and among different muscle groups of the assisted lower limb (kA) or the independent lower limb (kI). In particular, all investigated muscles (soleus, medial gastrocnemius, vastus lateralis, rectus femoris, gluteus maxim us, tibialis anterior and medial hamstring; total n=49), primary extensor muscles (left and right soleus, medial gastrocnemius, vastus lateralis, rectus femoris, gluteus maxim us; total n=35), or primary flexor muscles (left and right tibialis anterior and medial hamstring; total n=20) were considered for analysis. Values are expressed as mean±standard deviation (SD). Differences were tested by Wilcoxon test. * $p<0.05$;  $p<0.01$; * $p<0.001$.

We then assessed standing conditions during which one lower limb (i.e. left side) achieved independent extension while the contralateral lower limb (i.e. right side) required external assistance. Similarly to the previous findings, higher EMG total power, lower pattern variability, lower maximum power variability, lower median frequency SD, and lower median frequency were detected from the limb achieving independent extension (FIG. 7). This trend showed more consistent statistical significance when all investigated muscles were pooled together for analysis.

The higher median frequency and median frequency SD values observed during assisted standing can be attributed, at least partially, to the sharper peak shape of the spinal cord evoked responses generated (FIG. 8), which results in relevant increments of the instantaneous median frequency. Conversely, the smoother peaks of spinal cord evoked responses detected during independent standing contain more power at lower frequencies and result in a smaller instantaneous median frequency modulation.

Ranking the effectiveness of EMG activity for standing.

The high classification accuracy for assisted versus independent standing provided by this EMG-based framework (FIG. 3) led to the development of a further computational step for ranking the effectiveness of muscle activation patterns generated for standing. We initially trained muscle-specific KNN models based on three different standing data sets related to different external assistance for standing. Classification accuracy was high (95.3% on average) for the KNN model trained with assisted and independent standing data set (FIG. 11), while lower accuracy was observed for the other two models, as shown in Table 2.

TABLE 2

Classification accuracy of the KNN models trained for each individual muscle with 3 different data sets related to different external assistance for standing.

| Training Dataset | Classification Accuracy (%) | | | | | | | | |
|---|---|---|---|---|---|---|---|---|---|
| | SOL | MG | TA | VL | RF | MH | GL | IL | Avg. |
| Hips and knees assisted - Hips and knees independent | 95.8 | 96.3 | 97.5 | 95.5 | 95.4 | 95.7 | 94.4 | 92.2 | 95.3 |
| One knee assisted - Hips and knees independent | 93.3 | 92.8 | 91.7 | 92.8 | 87.2 | 90.5 | 87.8 | 88.9 | 90.6 |
| Hips assisted and knees independent - Hips and knees independent | 78.8 | 82.6 | 79.9 | 78.9 | 77.9 | 81.0 | 78.3 | 85.0 | 80.3 |

Figure 10A:
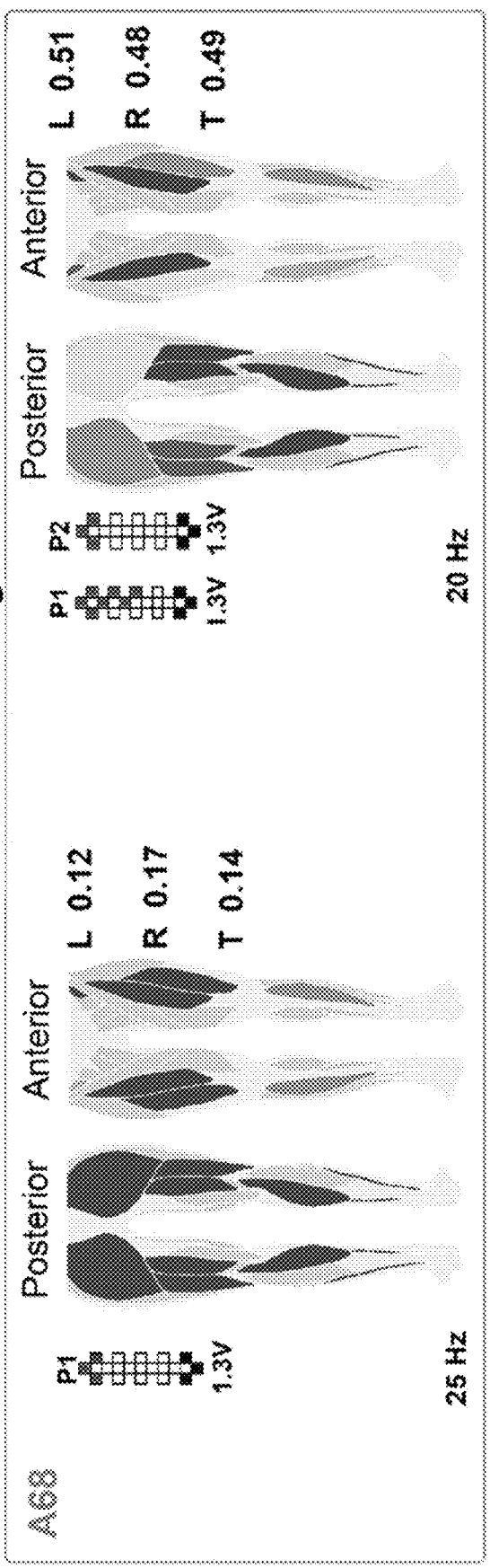
FIG. 10A displays a colormap representing the effectiveness of standing muscle activation. The effectiveness of standing muscle activation is ranked by the prediction algorithm as described herein. For each investigated muscle represented in the anatomical schematics, shades of red color rank activations labeled as assisted standing, while shades of blue color rank activations labeled as independent standing. Exemplary effects of different epidural stimulation parameters on muscle activation ranking during standing with external assistance for hips and knees extension. Average ranking score for the investigated muscles of the left (L) and right (R) lower limb, as well as for all muscles pooled together (total, T) are reported. Research participants' identification, stimulation amplitude, frequency and electrode configurations (cathodes in black, anodes in red, and inactive in white) are also reported.
Figure 10A:
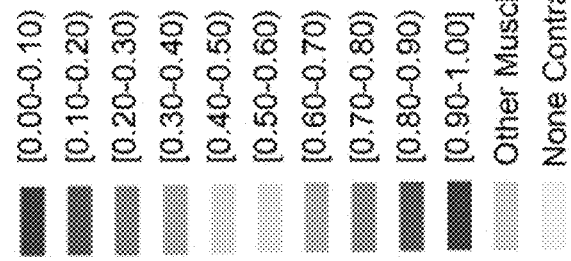
Figure 11:
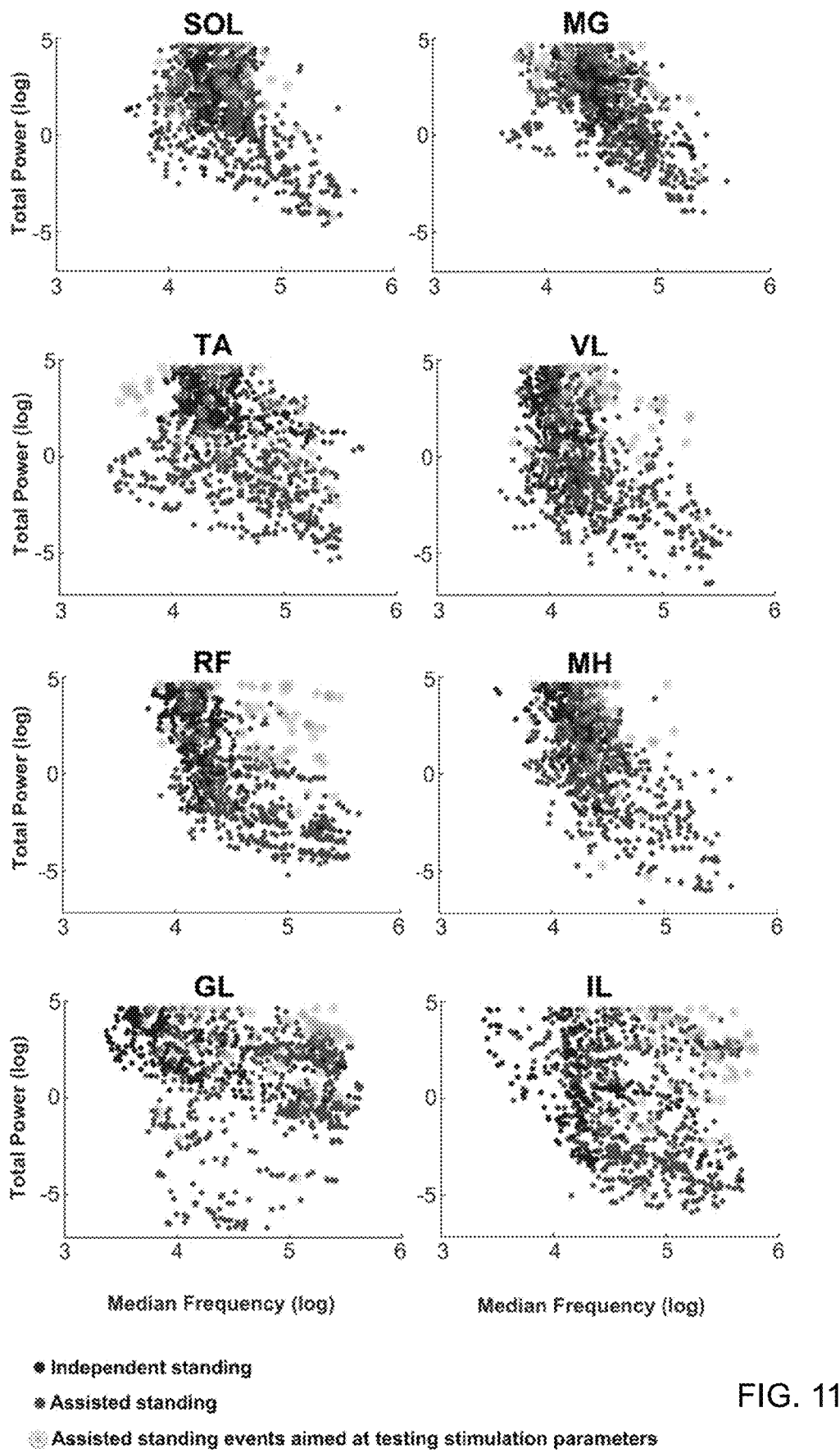
FIG. 11 is a series of charts for different muscles depicting features of the EMG data sets used to train classification and prediction algorithms. Two representative features (EMG total power and median frequency) of the EMG data sets used to train assisted (red) and independent (blue) standing KNN models are plotted against each other for each investigated muscle. Trends of assisted and independent standing data points are overall similar across muscles, while the distribution pattern shows some inter-muscle variability (i.e. between TA and GL). EMG data collected from 6 individuals during a total of 48 standing events aimed at testing the effectiveness of different stimulation parameters (green stars) were then fed to the prediction algorithm. While all these attempts resulted in assisted standing, the related EMG data points are spread across the plots, with some of them partially overlapping independent standing data points.

We then fed the prediction algorithm with a total of 48 standing events performed by 6 individuals while different stimulation parameters were tested to search for optimal stand-scES parameters (FIG. 11). The prediction algorithm correctly labeled as "assisted" (i.e. score between 0 and 0.5) 95.8% of the standing events considered. More importantly, its ranking scores varied substantially among stimulation parameters applied and investigated muscles. This shows that the prediction algorithm can accurately differentiate between the stimulation parameters that successfully target the extension of lower limb muscles for standing and the stimulation parameters that fail to achieve this goal. For example, participant A68 tested 9 different sets of scES parameters during the monitored standing session, obtaining average prediction scores ranging between 0.14 and 0.49 (FIG. 10A). In particular, during the standing attempt characterized by the lower score, only R IL and TA muscles showed EMG activity characteristics closer to independent standing. On the other hand, the standing attempt with the higher score was characterized by independent standing-like EMG characteristics of several muscles (i.e. posterior thigh muscles and anterior muscles of the left lower limb). Also, EMG activity score of bilateral plantar flexor muscles was low in both standing conditions.

Figure 10B:
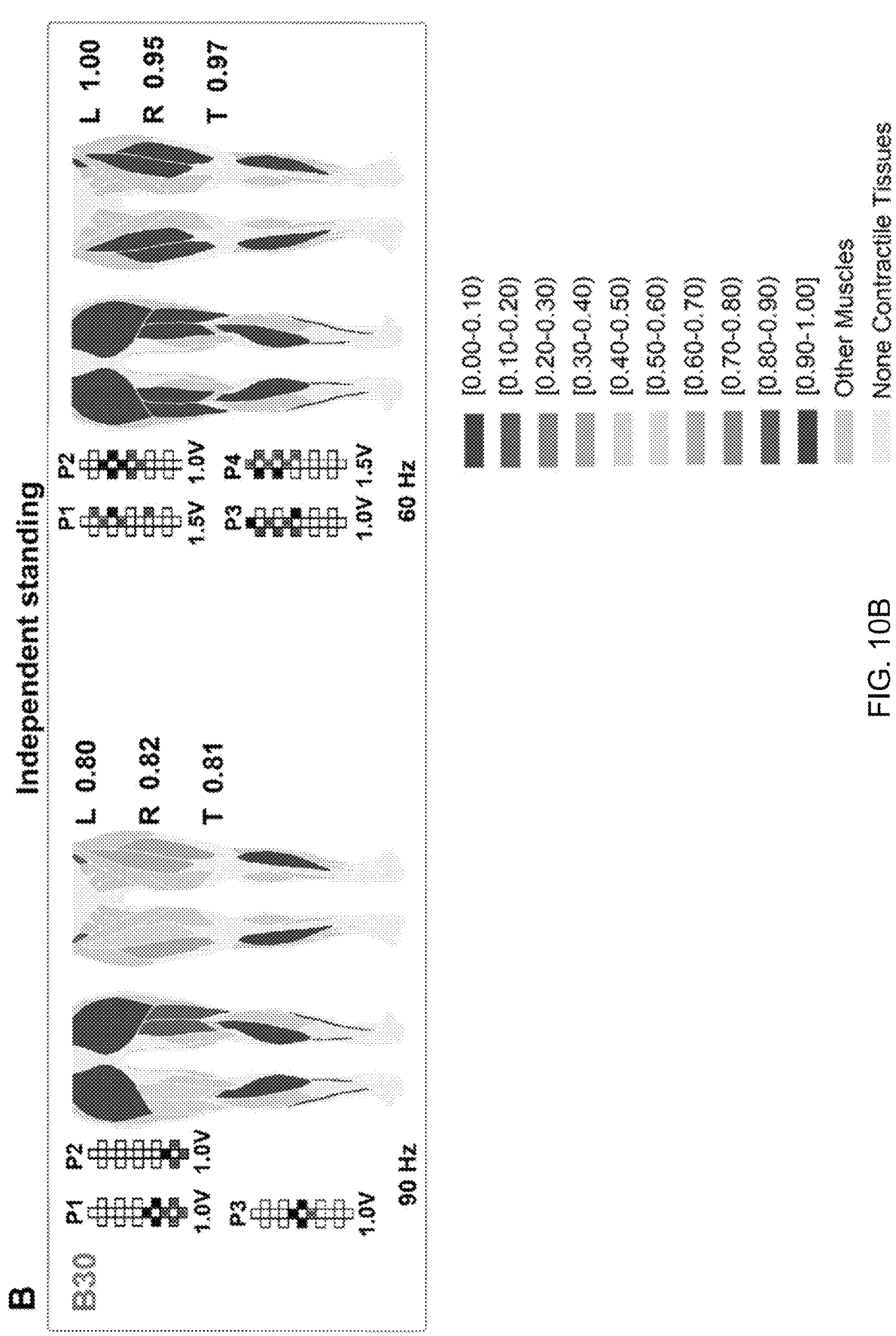
FIG. 10B displays a colormap representing the effectiveness of standing muscle activation. The effectiveness of standing muscle activation is ranked by the prediction algorithm as described herein. For each investigated muscle represented in the anatomical schematics, shades of red color rank activations labeled as assisted standing, while shades of blue color rank activations labeled as independent standing. Exemplary effects of different epidural stimulation parameters on muscle activation ranking during standing with independent lower limbs extension. Average ranking score for the investigated muscles of the left (L) and right (R) lower limb, as well as for all muscles pooled together (total, T) are reported. Research participants' identification, stimulation amplitude, frequency and electrode configurations (cathodes in black, anodes in red, and inactive in white) are also reported.
Figure 10C:
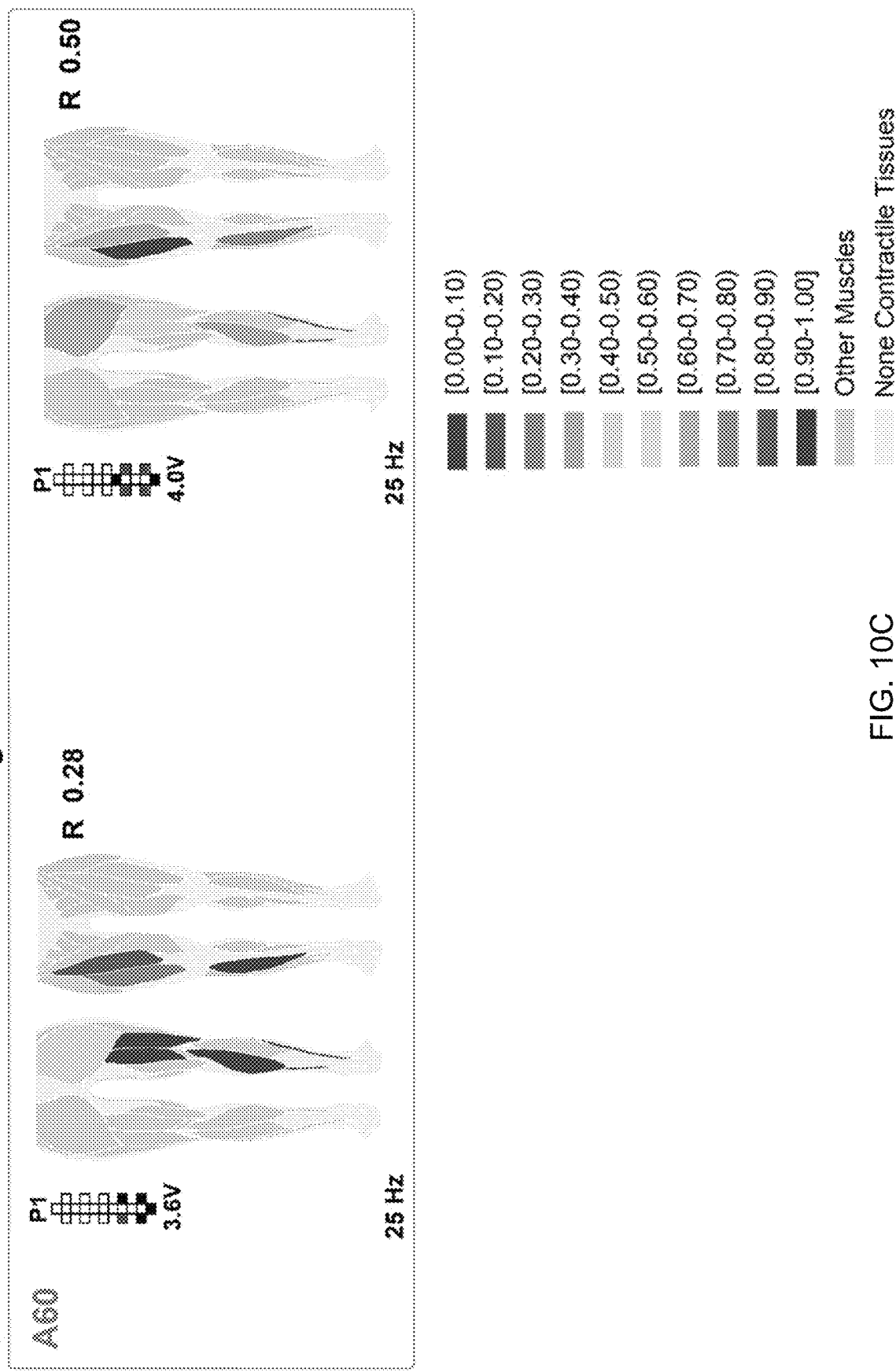
FIG. 10C displays a colormap representing the effectiveness of standing muscle activation. The effectiveness of standing muscle activation is ranked by the prediction algorithm as described herein. For each investigated muscle represented in the anatomical schematics, shades of red color rank activations labeled as assisted standing, while shades of blue color rank activations labeled as independent standing. Exemplary effects of different epidural stimulation parameters on muscle activation ranking during standing with one lower limb assisted (right side) while the contralateral limb achieved independent extension. Average ranking score for the investigated muscles of the left (L) and right (R) lower limb, as well as for all muscles pooled together (total, T) are reported. Research participants' identification, stimulation amplitude, frequency and electrode configurations (cathodes in black, anodes in red, and inactive in white) are also reported.

The disclosed prediction algorithm can also be used for ranking the effectiveness of EMG activity collected during standing with different amount of external assistance. For instance, it correctly labeled two standing events as "independent", and suggested that independent standing can be achieved even when the activation characteristics of few muscles are ranked as "assisted" (FIG. 10B). Also, when the algorithm is trained with the proper data set (data collected during standing with one lower limb assisted and the contralateral one generating independent extension, and during independent standing), it can rank the effectiveness of EMG activity generated by the lower limb assisted for knee extension (i.e. right side) while the other leg maintained independent extension (left side) (FIG. 10C).

Discussion

In this study, we developed a novel data processing framework for EMG activity promoted by spinal epidural stimulation during standing in individuals with severe SCI. This approach allowed us to uncover physiological characteristics of neuromuscular activation resulting in independent standing with self-assistance for balance. Additionally, we showed that, for each investigated muscle, the machine learning algorithm can rank the effectiveness of EMG activity generated for standing. These findings have implications in the context of mechanisms of motor pattern generation, and can contribute to the selection of scES parameters to facilitate the clinical translation of scES for standing motor rehabilitation.

Frequency-domain EMG features have been widely considered to study central motor control strategies during voluntary muscle activation, and the more recent development of technology for decomposing surface EMG signals has resulted in further insights on this topic. On the other hand, EMG spectral features have been substantially neglected when the generation of activation patterns is promoted by scES. Gerasimenko and colleagues proposed a qualitative interpretation of spectral analysis (by FFT) performed on EMG signals collected from flexor and extensor muscles during stepping with scES. In particular, they suggested that the dominant spectral peaks related to the stimulation frequency and its harmonics observed during the extension phase in extensor muscles reflected a predominance of monosynaptic-evoked responses. Conversely, the lack of consistent dominant peaks detected from the tibialis anterior muscle during the flexion phase of the gait cycle was interpreted as a predominance of polysynaptic-evoked responses. The marked dominant FFT spectral peaks related to the epidural stimulation frequency have been often interpreted as features without relevant physiological meaning, thus discouraging further efforts aimed at quantifying scES-promoted EMG spectral parameters. Our approach was initially focused on understanding which spectral analysis method is more effective for identifying frequency-domain EMG features that characterize standing promoted by scES. This is important because, for example, FFT presents some intrinsic limitations such as poor time resolution, assuming the stationarity of EMG signal, and being unable to localize frequency content of the signal in the time domain, which may result in insufficient representation of the frequency content of scES-promoted muscle activation. Our results suggest that CWT is a spectral analysis method that can provide relevant frequency content not related to scES frequency (FIG. 2) as well as features resulting in the most accurate classification of assisted and independent standing (FIG. 3B). This may be due to its high time and frequency resolution by decomposing the signal using numerous multi-resolution wavelets, which leads to an accurate characterization of the short time component within non-stationary signals. Conversely, the resolution of STFT in time and frequency domain depends on the selected window size: longer window size increases the frequency resolution but impairs time resolution, which is not ideal for non-stationary signals like EMG.

Figure 8:
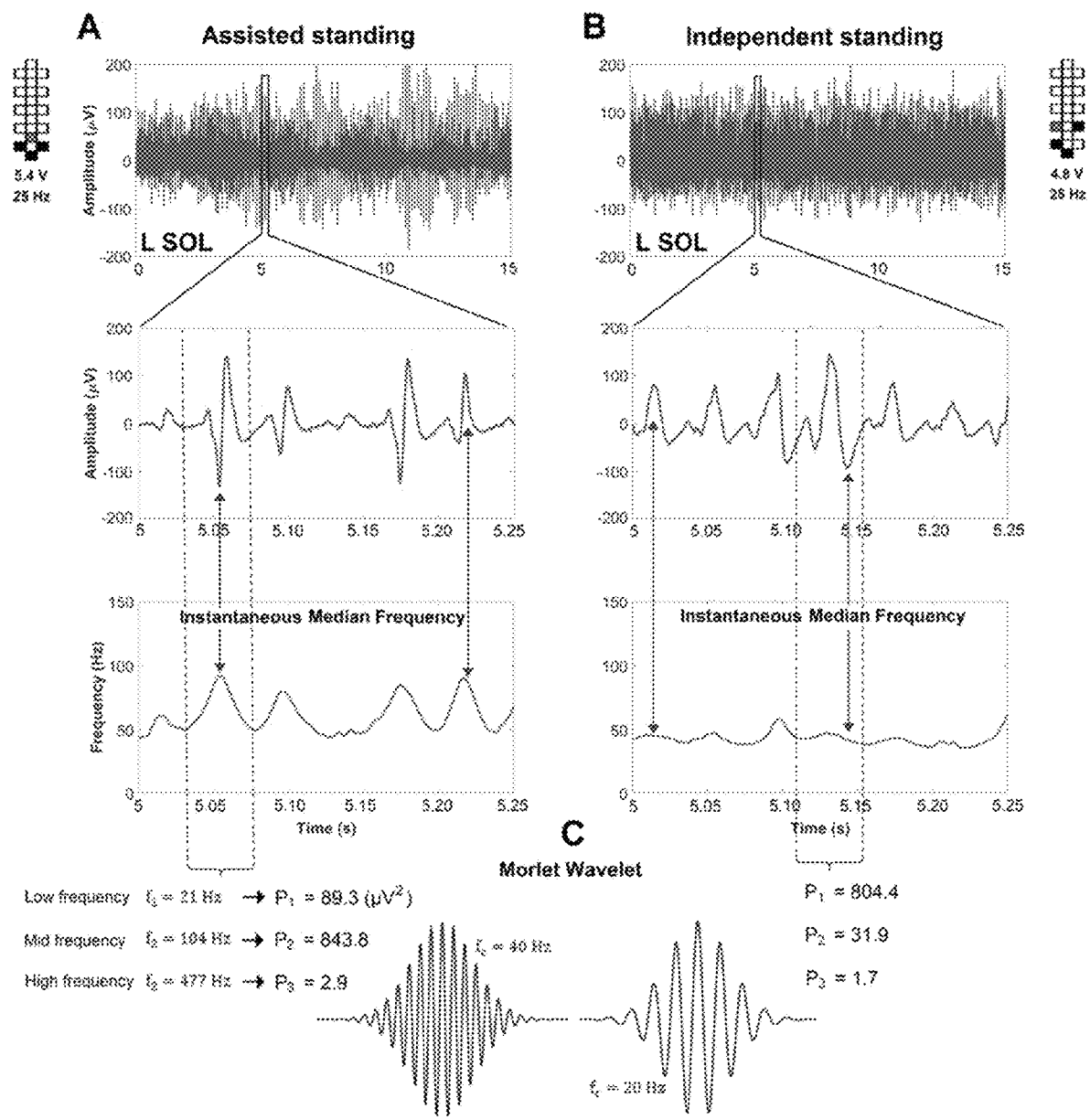
FIG. 8 depicts representative spinal cord evoked responses collected during assisted and independent standing. EMG activity collected from the left soleus (L SOL) muscle of research participant A45 (A) during standing with external assistance for hips and knees extension and (B) during standing with independent lower limb extension. Spinal cord evoked responses and instantaneous median frequency calculated by continuous wavelet transform are reported for EMG activity included in the windows entered in the top panels. (C) Exemplary Morlet wavelet signals with high (40 Hz, left) and low (20 Hz, right) central frequency (fc). The signal power at low (21 Hz), mid (104 Hz) and high (477 Hz) frequency bins is calculated for the spinal cord evoked responses highlighted by the dashed lines. Signal power collected during assisted standing is more concentrated at the mid frequency bin, while signal power collected during independent standing is more concentrated at the low frequency bin. Stimulation amplitude, frequency and electrode configuration (cathodes in black, anodes in red, and inactive in white) are reported for the two standing conditions.

To date, little is known about the characteristics of scES-promoted muscle activation resulting in the recovery of independent standing with self-assistance for balance after clinically motor complete SCI. We previously observed that the alternation between EMG bursts and little EMG activity (i.e. FIG. 1C, bottom) results in poor standing pattern and the need of external assistance. Conversely, overall continuous (i.e. non-rhythmic) co-activation of several lower limb muscles was demonstrated when motor complete SCI individuals were able to maintain independent lower limb extension using spinal cord stimulation. Here, we identified additional EMG features that can discriminate the effectiveness of EMG activity for standing beyond the mere variability of the EMG pattern over time. In particular, independent standing events were promoted by EMG activity characterized by lower median frequency, lower variability of median frequency, lower variability of instantaneous maximum power as well as higher total power as compared to assisted standing (FIGS. 4A, 4B, 4C, 5 and 7). The frequency-domain features can differentiate assisted and independent standing also when the raw EMG signals are both overall continuous and demonstrate similar amplitude (FIGS. 4 and 8). The higher median frequency and higher variability of median frequency detected during assisted standing reflect, at least partially, the sharper peaks of evoked responses, which carry more power at higher frequencies (FIG. 8). On the other hand, the smoother peaks of evoked responses detected during independent standing do not induce relevant increments in instantaneous median frequency. Without being bound by theory, partial desynchronization of motor units and/or greater involvement of polysynaptic responses, among others, may explain the smoother peaks of evoked responses detected during independent standing.

Presently, the prevailing view is that scES facilitates motor pattern generation by recruiting primarily large myelinated fibers associated with somatosensory information, and particularly with proprioceptive and cutaneous feedback circuits, at their entry into the spinal cord as well as along the longitudinal portions of the fiber trajectories, altering the excitability of lumbosacral spinal circuits. This more functional excitability state, in turn, enables the spinal circuitry to use somatosensory information and residual supraspinal input as sources of control for generating motor patterns appropriate for standing and stepping. Simulation parameters play a crucial role in determining extent and proportion of the modulation of sensory-motor pathways impacted by scES. For example, previous studies proposed that different stimulation frequencies may access different inhibitory and/or excitatory pathways within spinal circuitry, and that higher stimulation frequencies may promote a progressive integration of additional afferent inputs through the greater involvement of interneurons. Hence, an effort was devoted to understand whether the differences in EMG features observed in the present study between assisted and independent standing, and particularly the frequency-domain features, were associated with the application of different scES frequencies. Interestingly, the average stimulation frequencies delivered during assisted and independent standing were very similar (see description of FIGS. 5 and 9). Moreover, consistent differences in EMG features were also observed between the one lower limb achieving independent extension and the contralateral lower limb requiring external assistance, while the same spinal cord stimulation was applied (FIG. 7). Taken together, these findings further suggest that the characteristics of muscle activation result from the complex interaction among the stimulation parameters applied, the somatosensory information as well as any residual supraspinal input integrated by the spinal circuitry, and the characteristics of its extensive, individual-specific reorganization after SCI.

Figure 3:
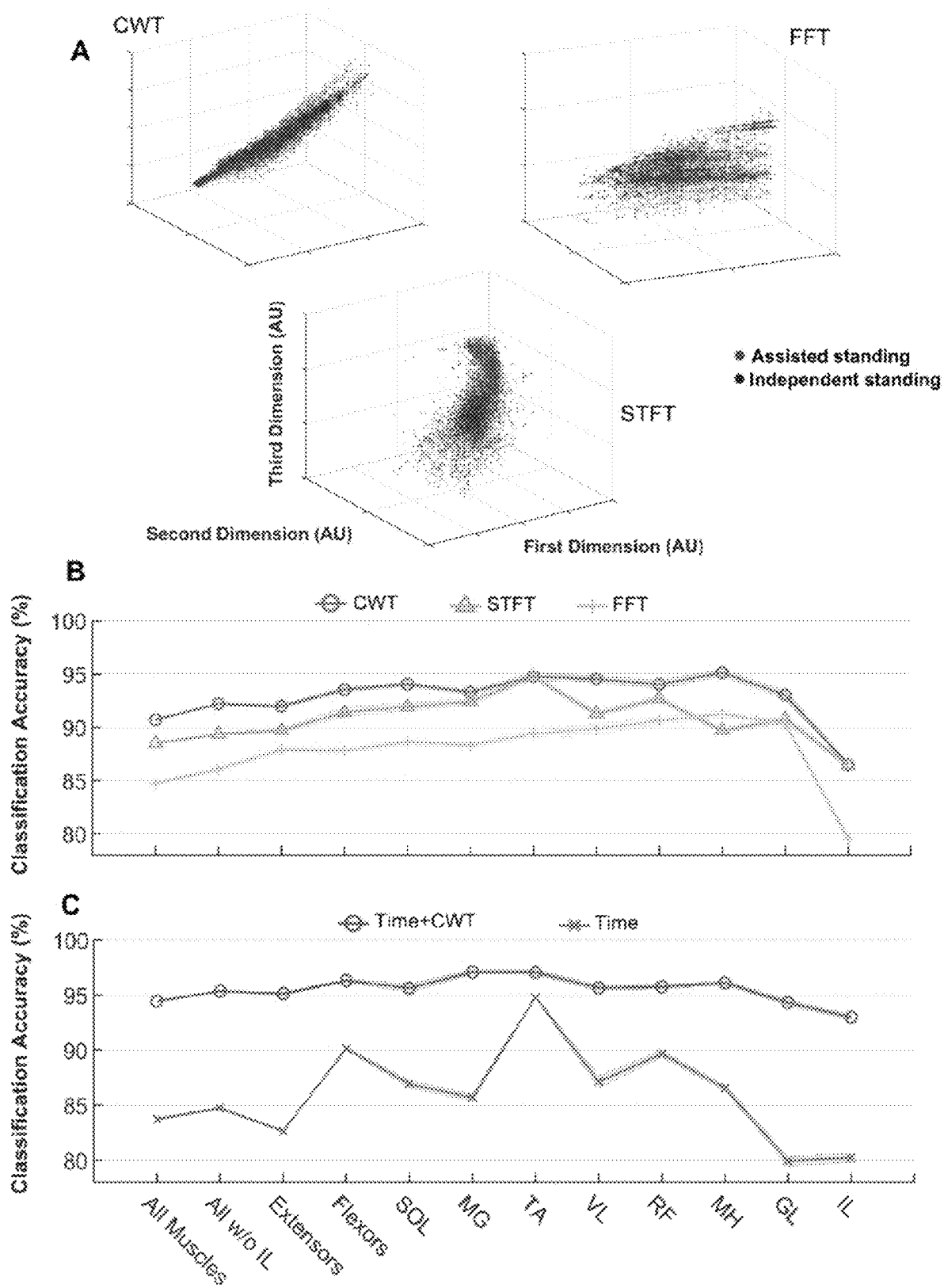
FIG. 3 depicts EMG-based classification of assisted vs independent standing. (A) First three dimensions of EMG standing data points (blue: independent standing, n=2032; red: assisted standing, n=4984) after normalization, dimension reduction and logarithmically transforming the spectral feature vectors extracted from Continuous Wavelet Transform (CWT), Short-Time Fourier Transform (STFT) and Fast Fourier Transform (FFT). Independent standing: independent lower limb extension and self-assistance for balance; assisted standing: external assistance for hip and knee extension and self-assistance for balance. K-nearest neighbor classification accuracy of the standing condition (assisted or independent standing) provided by feature vectors extracted from CWT, STFT and FFT (B), and by time-domain features only or by the integration of time-domain features and CWT-extracted features (C), when considering all investigated muscles (left and right soleus (SOL), medial gastrocnemius (MG), vastus lateralis (VL), rectus femoris (RF), gluteus maximus (GL), tibialis anterior (TA), medial hamstring (MH), iliopsoas (IL); all muscles except left and right IL; primary extensor muscles (left and right SOL, MG, VL, RF, GL); primary flexor muscles (left and right TA and MH); and each investigated pair of muscles separately (left and right SOL, MG, TA, VL, RF, MH, GL, IL).

The integration of novel CWT-derived features with EMG total power and pattern variability enabled the proposed machine learning (KNN) algorithm to accurately classify assisted and independent standing (FIG. 3). We took advantage of this high classification accuracy to develop a prediction algorithm capable of ranking the activation effectiveness of the investigated muscles for standing (FIGS. 10A-10C). This approach results in a quasi-real time feedback on the effectiveness of scES-promoted muscle activation for standing, which can support researchers and clinicians during the process of selection of stimulation parameters. For example, the data reported in FIG. 10A suggests that left and right plantar flexors presented poor activation with both sets of stimulation parameters, being one of the possible factors limiting the achievement of independent standing. The instant invention can thus improve and facilitate the adjustment of stimulation parameters for optimizing muscle activation. For instance, information on the individualized map of motor pools activation may be retrieved and used to determine the electrode field of an additional interleaving program aimed at targeting primarily the location of the spinal circuitry related to plantar flexors. Then, a much smaller cohort of cathode-anode combinations as well as amplitude and frequency values can be tested, thus increasing the probability of achieving an improved activation patter in a reduced amount of time. This is of particular interest considering that over 40 million different combinations of electrode configurations are potentially available when using a 16-electrode array, and that minor adjustments in the electrode configuration may or may not affect significantly standing motor pattern. Another contribution of the present invention is that it can suggest which of the tested set of stimulation parameters promotes the activation pattern more effective for the desired muscle action, e.g., independent standing. This can be relevant when different sets of parameters result in the same need of external assistance (i.e. total score of FIGS. 10A and 10C), and the decision on which parameters to apply for stand training should be made.

In conclusion, we have demonstrated that the proposed data analysis framework can characterize time- and frequency-domain EMG features resulting in the recovery of independent standing with self-assistance for balance in individuals with motor complete SCI using spinal cord epidural stimulation. This allowed us to develop and train a machine learning algorithm capable of ranking the effectiveness of muscle-specific activation for standing, which may facilitate the process of selection of stimulation parameters for standing motor rehabilitation.

Methods

Participants

Eleven individuals with chronic, clinically motor complete or sensory and motor complete SCI individuals are included in this study (Table 3). Prior to epidural stimulator implantation, the International Standards for Neurological Classification of Spinal Cord Injury was used for classifying the injury using the ASIA (American Spinal Injury Association) Impairment Scale (AIS). The research participants were recruited over 6 years (2009 to 2015), and were enrolled into interventional studies focused on either the facilitation of standing and stepping or the recovery of cardiovascular function.

TABLE 3

Clinical characteristics of the research participants.

| ID | Age (yrs) | Sex | Duration of Injury (Yrs) | Neurological Level | AIS Grade | Sensory (T10-S5, core out of 24) | | | | Motor (lower extremity) | | Anal sensation | Anal contraction | Intervention |
| --- | --- | --- | --- | --- | --- | --- | --- | --- | --- | --- | --- | --- | --- | --- |
| | | | | | | LT L | PP L | LT R | PP R | L | R | | | |
| B13 | 33 | M | 4.2 | C7 | B | 10 | 10 | 10 | 8 | 0 | 0 | Yes | No | Motor #1 |
| B07 | 24 | M | 3.4 | T2 | B | 15 | 11 | 18 | 10 | 0 | 0 | Yes | No | Motor #1 |
| A45 | 24 | M | 2.2 | T4 | A | 0 | 0 | 0 | 0 | 0 | 0 | No | No | Motor #1 |
| A53 | 27 | M | 2.3 | T4 | A | 0 | 0 | 0 | 0 | 0 | 0 | No | No | Motor #1 |
| B23 | 32 | M | 3.3 | C5 | B | 8 | 0 | 10 | 0 | 0 | 0 | Yes | No | Motor #2 |
| A59 | 26 | M | 2.5 | T4 | A | 0 | 0 | 0 | 0 | 0 | 0 | No | No | Motor #2 |
| B30 | 22 | F | 3.3 | T1 | B | 17 | 5 | 17 | 9 | 0 | 0 | Yes | No | Motor #2 |
| A60 | 23 | M | 3.1 | T4 | A | 0 | 0 | 0 | 0 | 0 | 0 | No | No | Motor #2 |
| A68 | 35 | M | 3.8 | C4 | A | 0 | 0 | 0 | 0 | 0 | 0 | No | No | Cardiovascular |
| A41 | 24 | M | 7.2 | C4 | A | 0 | 0 | 0 | 0 | 0 | 0 | No | No | Cardiovascular |
| B21 | 31 | M | 7.0 | C4 | B | 1 | 1 | 0 | 0 | 0 | 0 | Yes | No | Cardiovascular |

In Table 3, the sensory score was designated by light-touch (LT) and pinprick (PP) of the left (L) and right (R) lower limb, below the level of injury. Neuro level: neurological level of the lesion; AIS: American Spinal Injury Association (ASIA) Impairment Scale. Each research participant was enrolled in an interventional study focused on either the facilitation of standing and stepping (Motor #1 and Motor #2, respectively) or the recovery of cardiovascular function (Cardiovascular).

Surgical Implantation of Electrode Array and Stimulator

Figure 6:
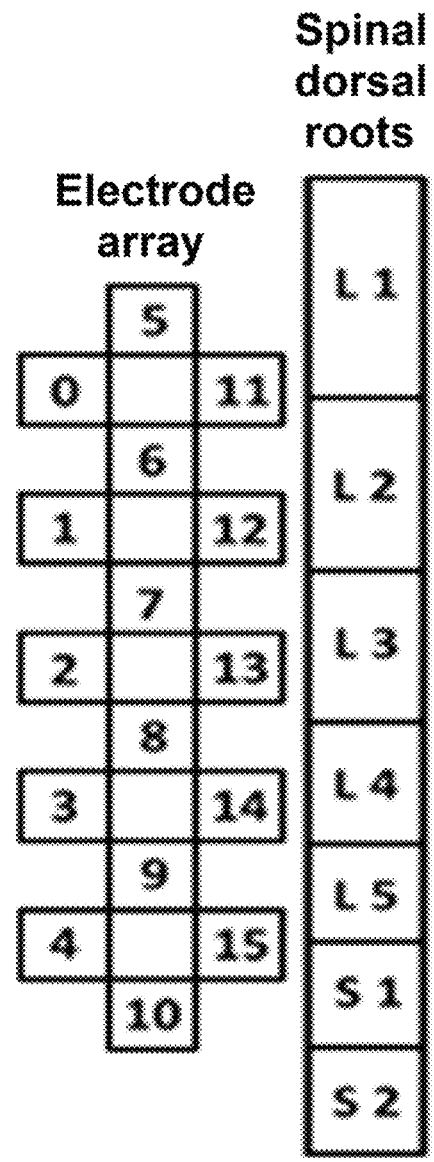
FIG. 6 is a schematic of a 16-electrode array configuration relative to spinal dorsal roots

The epidural spinal cord stimulation unit (Medtronic, RestoreAdvanced) and the 16-electrode array (Medtronic, 5-6-5 Specify) were surgically implanted in the eleven research participants. The electrode array was positioned over the midline of the exposed dura, in correspondence of spinal segments L1-S1/S2 (FIG. 6). EMG recordings from leg muscles were obtained intraoperatively during spinal stimulation at 2 Hz using midline, left and right electrode pairs in order to localize the optimal placement of the array. The wire leads were then internalized and tunneled subcutaneously to the abdomen and connected to the neurostimulator.

Experimental Procedures

Experimental sessions devoted to the assessment of motor patterns generated during standing were performed over ground in a full bodyweight bearing condition, using a custom-designed standing apparatus. This standing apparatus is comprised of horizontal bars anterior and lateral to the individual that were used for upper extremity support and balance assistance as needed. Mirrors were placed in front of the participants and laterally to them, in order to provide visual feedback on their body position. Four individuals (B23, A59, B30, A60) performed standing also using a walker that was fixed to a wider aluminum frame base, a regular walker, or holding the hands of a trainer (hand-hold). Research participants always self-assisted balance control using their upper limbs.

scES was applied while the participant was seated. The sit to stand transition was performed with the research participants using their upper limbs to partially pull themselves into a standing position, and trainers positioned at the pelvis and knees manually assisting as needed the transition. When a stable standing position was achieved, if the knees or hips flexed beyond the normal standing posture, external assistance was provided at the knees distal to the patella to promote extension, and at the hips below the iliac crest to promote hip extension and anterior tilt. In particular, external facilitation was provided either manually by a trainer or by elastic cords, which were attached between the two vertical bars of the standing apparatus.

Selection of scES Parameters for Standing

A subset of scES parameters aimed at facilitating standing were initially identified based on information obtained from previous assessments performed on the same research participants in supine position as well as from the literature. In particular, different bipolar and wide-field electrode configurations were applied using 2 Hz stimulation frequency (similarly to what has been previously reported) in order to define individualized maps of motor pools activation. The interplay among electrode configuration, stimulation frequency and intensity was also examined to identify the combination of parameters that generated rhythmic locomotor-like activity. Additionally, we considered the fact that i) cathodes (active electrode) positioned caudally, and more caudally than anodes, were shown to possibly promote better motor patterns characteristic of standing behavior in clinically motor complete SCI individuals while lying supine and standing; wider electrode fields evokes non location-specific responses in both proximal and distal muscles. scES was initially delivered at a near-motor threshold stimulation amplitude that did not elicit directly lower limb movements in sitting. scES parameters were then adjusted during standing, for example unbalancing anodes and cathodes between the lateral columns of the electrode array to compensate activation differences between left and right lower limb, or adding interleaving stimulation programs to facilitate the activation of specific muscle groups. Also, stimulation frequency and amplitude were modulated synergistically in order to identify the higher stimulation frequency that elicited a continuous (non-rhythmic) EMG pattern effective to bear body weight.

Each research participant underwent one or two experimental sessions aimed at selecting appropriate scES parameters for standing prior to the beginning of stand training. Stimulation parameters were also adjusted throughout stand training. In particular, dedicated sessions were performed approximately every 2-4 weeks to monitor motor behavior and lower limb EMG activity while testing different stimulation parameters to contribute to their selection.

Activity-Based Interventions

The standing experimental sessions considered for the present study were performed using scES, and were carried out after scES implantation and prior to any training as well as after the different interventions defined for each of the three study groups, which are briefly described here below. All activity-based training protocols were performed with scES optimized for the task that was practiced.

Motor #1 (Described by Rejc and colleagues). Research participants underwent 81±1 sessions of full weight-bearing stand training (1 hour of standing, five sessions per week). Stand training was performed using the custom-designed standing apparatus previously described. Participants were encouraged to stand for as long as possible throughout the training session, with the goal of standing for 60 min with the least amount of assistance. Seated resting periods occurred when requested by the individuals. Following the completion of stand training and respective experimental sessions, the research participants performed 81±2 sessions of step training with body weight support (Innoventor, St. Louis, MO) on a treadmill (1 hour, five sessions per week). Body weight support, stepping speed and bouts duration were adapted to each individual to obtain appropriate stepping kinematics. Following a stepping bout, participants were encouraged to maintain standing. The research participants were also encouraged to practiced voluntary trunk and lower extremity movements with scES 5 days a week (1 hour per session).

Motor #2 (Described by Angeli and colleagues). The initial portion of the training protocol (81±6 sessions) consisted of one 1-hour training session per day for five days a week, and the trained motor task (standing or stepping) was alternated every session. During the second portion of the training protocol (79±6 sessions), one supplementary training session was added every two weeks to the weekly schedule, to result in two training sessions per day. The research participants were encouraged to volitionally contribute to the motor pattern generation during training. Research participants were also encouraged to practice voluntary trunk and lower extremity movements with scES 5 days a week (1 hour per session).

Cardiovascular This study protocol included three different interventions, which were performed in sequential order and were cumulative. Research participants presenting with persistent low resting blood pressure initially completed 83±3 two-hour sessions of daily scES aimed at increasing systolic blood pressure within 105 to 120 mm Hg, as reported by Harkema and colleagues. In addition to this task, they subsequently performed approximately 80 training sessions of voluntary trunk and lower extremity movements practice (5 days a week, 1 hour per session). Following the completion of voluntary movements training, research participants also included stand training in their daily activities. In particular, research participants completed 83±1 stand training sessions (5 days a week, 1 hour of standing per session).

Data Acquisition

EMG, ground reaction forces and kinematics data were recorded at 2000 Hz using a custom-written acquisition software (National Instruments, Austin, Tex.). EMG activity of right (R) and left (L) gluteus maximus (GL), medial hamstring (MH), rectus femoris (RF), vastus lateralis (VL), tibialis anterior (TA), medial gastrocnemius (MG) and soleus (SOL) was recorded by means of bipolar surface electrodes with fixed inter-electrode distance. Bilateral EMG from the iliopsoas (IL) was recorded with fine-wire electrodes. Two surface electrodes were placed symmetrically lateral to the electrode array incision site over the paraspinal muscles in order to record the stimulation artefacts, which were used as indicators of the stimulation onset (time points when the stimulus pulses were applied). Lower limb joint angles were acquired using a high-speed optical motion capture system (Motion Analysis, Santa Rosa, CA). Ground reaction forces were collected using a high-resolution pressure sensing mat (HR mat system, TEKSCAN, Boston, MA) or force platforms (Kistler Holding AG, Winterthur, Switzerland).

Data Analysis

Each standing event considered for analysis was characterized by consistent external assistance and stimulation parameters for a duration ranging between 40 and 70 seconds; the initial and final 5 seconds of each event were not considered for analysis. Each event was labeled as follow, based on whether hips and knees needed external assistance for maintaining standing or achieved independent extension: hips and knees assisted (assisted standing); hips assisted and knees independent; hips and knees independent (independent standing); one knee assisted and the contralateral knee independent.

The EMG processing framework consisted of several steps including spectral analysis, time- and frequency-domain features extraction, dimension reduction, classification and prediction, which are described here below.

EMG Time Domain Features

The EMG pattern variability was assessed by calculating the coefficient of variation (standard deviation/mean) of the EMG linear envelope obtained by filtering the rectified EMG signal through a low-pass digital filter (cutoff frequency: 4 Hz).

The EMG total power was calculated using the following equation:

$$P = \frac{1}{T}\int_0^T |x(t)|^2 dt \quad (1)$$

where $x(t)$ is the recorded EMG signal and T is the length of the signal. For each examined muscle, the total power was then normalized by the maximum value detected within each participant.

Spectral Analysis

In this study, we initially applied three signal analysis methods to the scES-promoted EMG activity, with the goal of identifying the analysis method that better differentiate conditions of assisted standing and independent standing based on the spectral information provided. Fast Fourier Transform (FFT) is one of the most commonly used methods for spectral analysis of EMG signals. It is characterized by high frequency resolution and poor time resolution, and cannot localize the frequency content of the signal in the time domain. Short-Time Fourier Transform (STFT) was designed to increase the time resolution of FFT by selecting a fixed-size window moving across the EMG signal. Finally, Continuous Wavelet Transform (CWT) has been designed to effectively localize the frequency content of non-stationary signals in both time and frequency domains by using size adjustable wavelets, which do not compromise time or frequency resolutions.

Frequency Domain Features

Power spectral density (PSD) of FFT, STFT spectrogram (s(t, f)) and CWT scalogram (p(f,t)) (using Morlet wavelet, $\psi_{f,t}(\tau)$) were calculated as reported in Equations 2 to 4, respectively.

$$FFT(f) = \int x(\tau)\exp(-j2\pi f\tau)d\tau, \quad (2)$$

$$PSD(f) = |FFT(f)|^2$$

$$STFT(t, f) = \int w^*(\tau - t)x(\tau)\exp(-j2\pi f\tau)d\tau, \quad (3)$$

$$STFT \text{ Spectrogram: } s(t, f) = |STFT(t, f)|^2$$

$$CWT(f, t) = \int x(\tau)\psi_{f,t}^*(\tau)d\tau, \quad (4)$$

$$\text{Morlet wavelet: } \psi_{f,t}(\tau) = \frac{1}{\sqrt{f_0/f}}\psi(\tau - t/(f_0/f)),$$

$$\text{Wavelet scalogram: } p(f, t) = |CWT(f, t)|^2$$

where $f_0$ is the sampling frequency (2 kHz).

The STFT window size was selected at 0.3 seconds to increase the time resolution of FFT while minimally compromising the frequency resolution.

Mean frequency, median frequency, dominant frequency, and maximum power are the physiologically relevant features that were extracted from FFT output.

As for STFT and CWT, instantaneous values of mean frequency (IMNF), median frequency (IMDF), dominant frequency ($F_{max}(t)$) and maximum power ($P_{max}(t)$) were initially calculated as shown in Equations 5-8, and their average and standard deviation (SD) were considered as features for further analysis. In particular, EMG maximum power variability was assessed by calculating its coefficient of variation (SD/mean).

$$IMNF(t) = \frac{\sum_{j=1}^{M} f_j p(f_j, t)}{\sum_{j=1}^{M} p(f_j, t)} \quad (5)$$

$$\sum_{j=1}^{IMDF(t)} p(f_j, t) = \sum_{j=IMDF(t)}^{M} p(f_j, t) \quad (6)$$

$$F_{max}(t) = \text{argmax}_f(p(f, t)) \quad (7)$$

$$P_{max}(t) = \max_f(p(f, t)) \quad (8)$$

where M is the number of frequency bins.

Classification

All the calculated EMG feature values (predictors) were normalized to their maximum to remove the effects of their units in the classification step. The non-negative matrix factorization (NNMF) algorithm was applied to the normalized measurements for dimensionality reduction and the output values were logarithmically transformed in order to stabilize the variance. We then performed preliminary analysis to determine which algorithmic classification method resulted in the highest accuracy for classifying conditions of assisted standing versus independent standing based on the EMG features herein considered. In particular, K-nearest neighbor (KNN) performed better than Naïve Bayes, binary Support Vector Machine, and ensemble decision trees; therefore, KNN was the classification method applied in the present study.

The KNN classifier includes several parameters that need to be adjusted in order to achieve its best classification performance. These parameters include number of neighbors, distance measures, distance weights and standardization (centering and scaling the predictors). In order to find the optimized parameters for the classifier, the Bayesian optimization algorithm was used. The objective function for the optimization is log (1+Cross Validation Loss). The Cross Validation Loss is the ratio of misclassified observations during the cross validation step. The classification accuracy is calculated using 10-fold cross validation method and calculated as a percentage value of 1−Cross Validation Loss. The KNN classifier with the parameter optimization algorithm and the cross validation step were iterated 10 times and the average accuracy values and the 95% confidence intervals are reported.

Prediction

All calculated EMG feature vectors (e.g., frequency-domain features including IMNF, IMDF, $F_{max}(t)$ and $P_{max}(t)$, and averages and standard deviations of the same, as well as the time-domain features EMG total power and EMG pattern variability) included in the classification step were then used as a training dataset for the prediction part of the framework. In other embodiments, a subset of the listed EMG feature vectors may be used or different EMG features may be used as the training dataset.

A trained model is defined as a model that has captured the patterns in the training dataset. Based on these learnt patterns, the trained model can predict the class label (i.e. assisted or independent standing) for new observations that were not included in the training dataset. For this part of the study, we developed KNN models that are trained for each investigated muscle pair (e.g., left and right soleus) on three data sets related to the following different external assistance for standing: i) hips and knees assisted vs hips and knees independent; ii) one knee assisted vs hips and knees independent; iii) hips assisted and knees independent vs hips and knees independent. The models related to the first data set were then used to predict the class labels for the prediction dataset, which includes assisted standing events collected from 6 research participants during experimental sessions aimed at testing the effectiveness of different scES parameters for standing. We also exemplified the application of models related to the second data set. The output of the prediction step is a score value ranging from 0 and 1, which is the posterior probability $P(C|X_{new})$ of "independent standing" class C given a new observation $X_{new}$ (Eq. 9).

$$P(C \mid X_{new}) = \frac{\sum_{i=1}^{K} W(X_i) 1_{X_i = C}}{\sum_{i=1}^{k} W(X_i)} \quad (9)$$

Where K is the number of nearest neighbors to $X_{new}$, $X_i$ is the $i^{th}$ nearest neighbor, $W(X_i)$ is the weight of $X_i$ which is the distance value from $X_{new}$ and normalized based on the class prior probability, i.e. the frequency of the number of observations in one class in the training dataset. The $1_{X_i=C}$ function returns 1 if observation $X_i$ belongs to class C and 0 otherwise.

For each muscle, score values equal or less than 0.5 assign the given observation to the "assisted standing" class label, while values greater than 0.5 assign the observation to the "independent standing" class label. The number of neighbors for the prediction task is set to K=5; this keeps the classification accuracy high for all muscle pairs and allows comparison of the prediction scores between KNN models.

All EMG analysis steps are performed using MATLAB R2017b software and its Statistics and Machine Learning Toolbox.

Statistical Analysis

Statistical analysis was performed using GraphPad Prism (version 5.00 for Windows, GraphPad Software, San Diego, California, USA). A p value<0.05 was considered statistically significant. The distribution of quantitative EMG variables was tested for normality using the Kolmogorov-Smirnov test, and the parametric or non-parametric tests reported below were applied accordingly. The effect of external assistance for standing on the EMG features considered (total power, pattern variability, maximum power variability, median frequency, median frequency standard deviation (SD)) was tested on all muscles investigated with surface EMG pooled together (left and right SOL, MG, TA, MH, VL, RF, GL), on primary extensor muscles (left and right SOL, MG, VL, RF, GL), and on primary flexor muscles (TA, MH). Additionally, we tested whether the stimulation frequency applied was significantly different among standing conditions with different amount of external assistance. In particular, paired comparisons between standing conditions of hips assisted—knees assisted and hips assisted—knees independent (subjects number=8) were performed by Wilcoxon test. Also, comparisons among standing with hips assisted—knees assisted, hips assisted—knees independent, and hips independent—knees independent (subjects number=5) were performed by either Repeated Measures Anova (and following multiple comparisons by Bonferroni's post hoc test) or by Friedman Test (and following multiple comparisons by Dunn's post hoc test). Finally, when one lower limb (i.e. left side) achieved independent extension while the contralateral limb (i.e. right side) required external assistance for knee extension, paired comparisons (subjects number=7) between the assisted and independent side were performed by Wilcoxon test.

The disclosed machine learning algorithm may be embodied in computer program instructions stored on a non-transitory computer readable storage medium configured to be executed by a computing system. The computing system would be arranged as typically known in the art, including a processor in communication with a memory, and a network interface. Power, ground, clock, and other signals and circuitry are not discussed, but will be generally understood and easily implemented by those ordinarily skilled in the art. The processor, in some embodiments, is at least one microcontroller or general purpose microprocessor that reads its program from memory. The memory, in some embodiments, includes one or more types such as solid state memory, magnetic memory, optical memory, or other computer-readable, non-transient storage media. In certain embodiments, the memory includes instructions that, when executed by the processor, cause the computing system to perform a certain action. In some embodiments, the action is receiving a diagnostic signal collected during the application of the scES pattern, extracting, using a signal analysis method, at least one feature from the diagnostic signal, and classifying, using a machine learning model, the diagnostic signal as characteristic of a desired muscle action or characteristic of a muscle action other than the desired muscle action, wherein the classifying is based at least in part on the at least one feature. The computing system also preferably include a network interface connecting the computing system to a data network, such as, for example, the Internet or a local area network, for electronic communication of data. In certain embodiments, the processor includes one or more processors and the memory includes one or more memories.

In some embodiments, the computing system is defined by one or more physical computing devices as described above. In other embodiments, the computing system may be defined by a virtual system hosted on one or more physical computing devices as described above.

While the disclosed systems and methods have been described primarily in terms of independent standing and assisted standing, it should be understood that other muscle actions may be evaluated using similar techniques. For example, EMG signals may be collected during independent and assisted transitions from a standing position to a seated position during application of scES, relevant features extracted via signal analysis methods, and a machine learning algorithm trained to differentiate between EMG signals characteristic of independent and assisted transitions.

Various aspects of different embodiments of the present disclosure are expressed in paragraphs X1, X2, and X3 as follows:

X1: One embodiment of the present disclosure includes a method for determining a spinal cord epidural stimulation (scES) pattern effective in promoting muscle action, comprising: collecting a first diagnostic signal from at least one muscle during performance of a first muscle action during scES; collecting a second diagnostic signal from the at least one muscle during performance of a second muscle action during scES; extracting at least one feature from the first diagnostic signal and extracting the same at least one feature from the second diagnostic signal; training a machine learning model to distinguish between diagnostic signals characteristic of the first muscle action and diagnostic signals characteristic of the second muscle action based at least in part on the at least one feature; and classifying, using the machine learning model, a third diagnostic signal collected from the at least one muscle during scES as representative of the first muscle action or the second muscle action.

X2: Another embodiment of the present disclosure includes a method for evaluating a spinal cord epidural stimulation (scES) pattern for efficacy in promoting a first muscle action, the method comprising: applying a scES pattern to an individual; collecting a diagnostic signal from at least one muscle of the individual during the application of the scES pattern; and classifying, using a machine learning model, the diagnostic signal as representative of a first muscle action or representative of a second muscle action; wherein the machine learning model is trained distinguish between diagnostic signals characteristic of the first muscle action and diagnostic signals characteristic of a second muscle action.

X3: A further embodiment of the present disclosure includes a non-transitory computer readable storage medium having computer program instructions stored thereon that, when executed by a processor, cause the processor to perform the following instructions: receiving a diagnostic signal collected during the application of a pattern of spinal cord epidural stimulation (scES) to a subject; extracting, using a signal analysis method, at least one feature from the diagnostic signal; classifying, using a machine learning model, the diagnostic signal as characteristic of a desired muscle action or characteristic of a muscle action other than the desired muscle action, wherein the classifying is based at least in part on the at least one feature.

Yet other embodiments include the features described in any of the previous paragraphs X1, X2, or X3 as combined with one or more of the following aspects:

Wherein the first diagnostic signal and second diagnostic signal are EMG signals.

Wherein the diagnostic signal is an electromyography (EMG) signal.

Wherein the diagnostic signal is an electromyography (EMG) signal obtained from at least one muscle of the subject.

Wherein the feature is at least one of EMG total power, EMG pattern variability, IMNF, IMDF, $F_{max}(t)$, and $P_{max}(t)$.

Wherein the at least one feature is at least one of EMG total power, EMG pattern variability, IMNF, IMDF, $F_{max}(t)$, and $P_{max}(t)$.

Wherein the at least one feature is a plurality of EMG total power, EMG pattern variability, IMNF, IMDF, $F_{max}(t)$, and $P_{max}(t)$.

Wherein the at least one feature is a mean or standard deviation of at least one of EMG total power, EMG pattern variability, IMNF, IMDF, $F_{max}(t)$, and $P_{max}(t)$.

Wherein said extracting comprises applying at least one signal analysis method to the first diagnostic signal and applying the same at least one signal analysis method to the second diagnostic signal.

Wherein the method further comprises extracting, using a signal analysis method, a feature from the diagnostic signal, and wherein the classifying is based at least in part on the feature.

Wherein the at least one signal analysis method is one of fast Fourier transform, short-time Fourier transform and continuous wavelet transform.

Wherein the at least one signal analysis method is continuous wavelet transform.

Wherein the first muscle action and the second muscle action are non-identical.

Wherein the first muscle action is an unassisted muscle action and wherein the second muscle action is an assisted muscle action.

Wherein the first muscle action is unassisted standing and wherein the second muscle action is assisted standing.

Wherein applying the scES pattern comprises applying a plurality of electrical stimulations, and wherein the feature is extracted, at least in part, between the applications of electrical stimulation.

Wherein the application of the pattern of scES to the subject comprises applying electrical stimulations to the subject at a frequency, and wherein the at least one feature is extracted, at least in part, between the applications of electrical stimulation.

The foregoing detailed description is given primarily for clearness of understanding and no unnecessary limitations are to be understood therefrom for modifications can be made by those skilled in the art upon reading this disclosure and may be made without departing from the spirit of the invention.

What is claimed is:

1. A method for determining a spinal cord epidural stimulation (scES) pattern effective in promoting muscle action, comprising:
   detecting a first diagnostic signal from at least one muscle of a subject during performance of a first muscle action during a first application of scES to the subject;
   detecting a second diagnostic signal from the at least one muscle of the subject during performance of a second muscle action during a second application of scES to the subject;
   extracting at least one feature from the first diagnostic signal and extracting the same at least one feature from the second diagnostic signal;
   classifying, using a machine learning model, a third diagnostic signal collected from the at least one muscle during a third application of scES to the subject as representative of the first muscle action or the second muscle action based at least in part on the at least one feature.

2. The method of claim 1, wherein the first diagnostic signal and second diagnostic signal are electromyography (EMG) signals.

3. The method of claim 1, wherein the machine learning model is trained to distinguish between diagnostic signals characteristic of the first muscle action and diagnostic signals characteristic of the second muscle action based at least in part on the at least one feature.

4. The method of claim 1, wherein the at least one feature is at least one of EMG total power, EMG pattern variability, instantaneous values of mean frequency (IMNF), instantaneous values of median frequency (IMDF), dominant frequency ($F_{max}(t)$), and maximum power ($P_{max}(t)$).

5. The method of claim 1, wherein said extracting comprises applying at least one signal analysis method to the first diagnostic signal and applying the same at least one signal analysis method to the second diagnostic signal.

6. The method of claim 5, wherein the at least one signal analysis method is one of fast Fourier transform, short-time Fourier transform and continuous wavelet transform.

7. The method of claim 1, wherein the first muscle action and the second muscle action are non-identical.

8. The method of claim 1, wherein the first muscle action is an unassisted muscle action and wherein the second muscle action is an assisted muscle action.

9. A non-transitory computer readable storage medium having computer program instructions stored thereon that, when executed by a processor, cause the processor to perform the following instructions:
receiving a diagnostic signal from at least one muscle of an individual during an application of a spinal cord epidural stimulation (scES) pattern to the individual; and
classifying, using a machine learning model, the diagnostic signal as representative of a first muscle action or representative of a second muscle action;
wherein the machine learning model is trained to distinguish between diagnostic signals characteristic of the first muscle action and diagnostic signals characteristic of a second muscle action.

10. The method of claim 9, wherein the diagnostic signal is an electromyography (EMG) signal.

11. The method of claim 9, further comprising extracting, using a signal analysis method, a feature from the diagnostic signal, and wherein the classifying is based at least in part on the feature.

12. The method of claim 11, wherein the application of the pattern of scES to the individual comprises application of electrical stimulations to the individual at a frequency, and wherein the at least one feature is extracted, at least in part, from the diagnostic signal between the applications of electrical stimulation.

13. A method for evaluating a spinal cord epidural stimulation (scES) pattern for efficacy in promoting a first muscle action, the method comprising:
receiving a diagnostic signal collected during an application of a pattern of spinal cord epidural stimulation (scES) to a subject;
extracting at least one feature from the diagnostic signal;
classifying, using a machine learning model, the diagnostic signal as characteristic of a desired muscle action or characteristic of a muscle action other than the desired muscle action, wherein the classifying is based at least in part on the at least one feature.

14. The method of claim 13, wherein the diagnostic signal is obtained from at least one muscle of the subject.

15. The method of claim 13, wherein the diagnostic signal is an electromyography (EMG) signal.

16. The method of claim 13, wherein the extracting is performed using a signal analysis method.

17. The method of claim 13, wherein the application of the pattern of scES to the subject comprises application of electrical stimulations to the subject at a frequency, and wherein the at least one feature is extracted, at least in part, from the diagnostic signal between the applications of electrical stimulation.

* * * * *